United States Patent
Jang et al.

(10) Patent No.: US 10,092,258 B2
(45) Date of Patent: Oct. 9, 2018

(54) X-RAY APPARATUS

(71) Applicant: SAMSUNG ELECTRONICS CO., LTD., Suwon-si (KR)

(72) Inventors: Kyoung-choul Jang, Suwon-si (KR); Woo-sup Han, Yongin-si (KR); Seung-hwan Lee, Seoul (KR); Jae-won Lee, Seoul (KR); Min-hyung Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 15/350,353

(22) Filed: Nov. 14, 2016

(65) Prior Publication Data
US 2017/0055924 A1 Mar. 2, 2017

Related U.S. Application Data

(63) Continuation of application No. 14/813,392, filed on Jul. 30, 2015, now Pat. No. 9,521,983.

(30) Foreign Application Priority Data

Jul. 30, 2014 (KR) .................. 10-2014-0097616
Mar. 4, 2015 (KR) .................. 10-2015-0030554

(51) Int. Cl.
*A61B 6/00* (2006.01)
*G03B 42/04* (2006.01)

(52) U.S. Cl.
CPC .......... *A61B 6/4429* (2013.01); *A61B 6/4283* (2013.01); *A61B 6/547* (2013.01);
(Continued)

(58) Field of Classification Search
CPC ... A61B 6/4233; A61B 6/4283; A61B 6/0414; A61B 6/4405; G03B 42/04; G03B 42/02; G03B 42/025; G03B 42/045
See application file for complete search history.

(56) References Cited

U.S. PATENT DOCUMENTS 4,416,020 A   11/1983  Wagner et al.
4,426,724 A *  1/1984  Cutter .................. G03B 42/025
                                                         378/181
(Continued)

FOREIGN PATENT DOCUMENTS

JP        4717155 B1    7/2011
KR   1020110018042 A    2/2011
(Continued)

OTHER PUBLICATIONS

"Harmony Series Rotating tray enclosures for portable DR Panels", Oct. 1, 2013 (Oct. 1, 2013), XP055232002, Retrieved from the Internet: URL: www.claymount.com [retrieved on Nov. 27, 2015].
(Continued)

*Primary Examiner* — Hoon Song
(74) *Attorney, Agent, or Firm* — Sughrue Mion, PLLC

(57) ABSTRACT

A bucky tray for an X-ray imaging apparatus includes a first plate on which an X-ray detecting device is mountable, and a second plate configured to be coupled to the first plate to be movable to at least one of a first location where the X-ray detecting device of a first size is accommodated and a second location where another X-ray detecting device of a second size is accommodated. The X-ray detecting device is configured to be mounted on the bucky tray.

22 Claims, 35 Drawing Sheets

(52) U.S. Cl.
CPC ........... *A61B 6/56* (2013.01); *G03B 42/04* (2013.01); *A61B 6/4233* (2013.01); *A61B 6/4291* (2013.01); *A61B 6/4464* (2013.01)

(56) References Cited

U.S. PATENT DOCUMENTS

| | | | |
|---|---|---|---|
| 7,014,362 B2 | 3/2006 | Beimier et al. | |
| 7,503,693 B2 | 3/2009 | Jahrling | |
| 7,857,511 B2* | 12/2010 | Hesl | A61B 6/4233 378/189 |
| 8,848,872 B2 | 9/2014 | Lee | |
| 8,985,851 B2 | 3/2015 | Kim | |
| 2006/0018427 A1 | 1/2006 | Pflaum | |
| 2009/0066204 A1 | 3/2009 | Reina et al. | |
| 2010/0220838 A1* | 9/2010 | Kobayashi | G03B 42/04 378/189 |
| 2011/0110494 A1* | 5/2011 | Lee | G03B 42/04 378/98 |
| 2011/0129273 A1* | 6/2011 | Jang | B65H 1/266 400/355 |
| 2013/0248725 A1 | 9/2013 | Kim | |
| 2013/0336453 A1 | 12/2013 | Park et al. | |

FOREIGN PATENT DOCUMENTS

| | | |
|---|---|---|
| KR | 10-1085196 B1 | 11/2011 |
| KR | 10-2013-0106623 A | 9/2013 |
| WO | 0133921 A1 | 5/2001 |

OTHER PUBLICATIONS

"Technical Publication SM-1103R3 Service Manual", Nov. 5, 2013 (Nov. 5, 2013), XP055232005, Retrieved from the Internet: URL: http://www.txr.com/2-Brochures/Tables/TXR_Multirad_Table-SM-1103R3i.pdf [retrieved on Nov. 27, 2015].
Communication dated Dec. 9, 2015, issued by the European Patent Office in counterpart European Application No. 15179033.4.
Communication dated Nov. 11, 2015, issued by the International Searching Authority in counterpart International Application No. PCT/KR2015/007915.
Drive Digital Imaging Datasheet [Online]. Quantum Medical Imaging, LLC, 2012 [retrieved on Nov. 6, 2015]. Retrieved from the Internet: http://www.nyimagingservice.org/wp-content/uploads/2012/12/12897-Quantum_DRive_DR_Upgrade_Sotutions.pdf.
Enhancements to Toshiba's Kalare X-Ray System Increase Workflow and Productivity [Online], Dec. 2, 2010, [retrieved on Nov. 6, 2015]. Retrieved from the Internet: URL: https://medical.toshiba.com/news/press-releases/2010/12/08/825.
Communication dated May 19, 2017 issued by the European Patent Office in counterpart Application No. 15 179 033.4.
Communication dated Jan. 30, 2018, issued by the State Intellectual Property Office in counterpart Chinese application No. 201580050063.0.

* cited by examiner

X-RAY APPARATUS

CROSS-REFERENCE TO RELATED APPLICATIONS

This is a continuation application of U.S. application Ser. No. 14/813,392 filed Jul. 30, 2015, which claims priority from Korean Patent Application No. 10-2014-0097616, filed on Jul. 30, 2014, and Korean Patent Application No. 10-2015-0030554, filed on Mar. 4, 2015, in the Korean Intellectual Property Office, the disclosures of which are incorporated herein in their entireties by reference.

BACKGROUND

1. Field

Apparatuses and methods consistent with exemplary embodiments relate to an X-ray imaging apparatus, and more particularly, to an X-ray imaging apparatus including a bucky that allows an X-ray detecting device to be detached therefrom.

2. Description of the Related Art

An X-ray imaging apparatus is used to identify an internal structure or a state of an object by irradiating X-rays onto the object and detecting an energy intensity distribution of the X-rays which have penetrated the object. The X-ray imaging apparatus can be used for medical examinations, and at security check points to identify an internal structure of an object or a piece of luggage.

For medical purposes, the X-ray apparatus has been widely used for chest radiography, abdominal film, frame film, sinography, neck soft tissue film, breast film, etc.

The X-ray imaging apparatus may include an X-ray detecting device configured to detect X-rays that have penetrated a human body or an object. The X-ray detecting device may be analog or digital. The digital X-ray detecting device has a high spatial resolution at an optimum level, and excellent time resolution and contrast resolution, and thus, provides a high quality image.

Recently, various sizes and types of the digital X-ray detecting devices have been developed, and, thus, apparatuses and methods are needed to easily accommodate the detectors of different sizes in the X-ray apparatus.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more exemplary embodiments include an X-ray imaging apparatus that allows adjustment of an arrangement location of a digital X-ray detecting device in a bucky according to an angle at which the digital X-ray detecting device is used.

One or more exemplary embodiments include an X-ray imaging apparatus including a bucky in which X-ray detecting devices of various sizes can be arranged.

According to an aspect of an exemplary embodiment, an X-ray imaging apparatus includes: an X-ray detecting device; an accommodation unit configured to accommodate the X-ray detecting device; and a bucky tray configured to be accommodated in and discharged from the accommodation unit, wherein the bucky tray includes: a base; and a first plate on which the X-ray detecting device is mounted and which is configured to rotate with respect to the base in a first state and a second state.

The X-ray imaging apparatus may further include a rotation plate fastened to a surface of the first plate and including a slide rail formed along a cylindrical direction of the rotation plate; and a guide provided on the base and configured to be inserted into the slide rail.

A center of the rotation plate may be eccentric with respect to a center of the base.

A center of the rotation plate may match a center of the base.

The X-ray imaging apparatus may further include one or more rotation sensors configured to sense a rotation of the rotation plate.

The rotation sensors may include a first rotation sensor and a second rotation sensor arranged apart from each other by a predetermined distance along the cylindrical direction of the rotation plate.

Each of the first rotation sensor and the second rotation sensor may be an optical encoder or a magnetic encoder.

The X-ray imaging apparatus may further include a detachment sensor configured to sense whether the X-ray detecting device is detached from the bucky tray.

The X-ray detecting device may include a first terminal, and the first plate may include a second terminal connected to the first terminal to connect the X-ray detecting device to the outside.

The X-ray imaging apparatus may further include a detector cable, an end of which is connected to the second terminal and other end of which is connected to the outside via a penetration hole in the base.

The X-ray imaging apparatus may further include a plurality of cable fasteners arranged in the base to prevent twisting of the detector cable by restricting a portion of a movement path of the detector cable.

The X-ray detecting device may be connected to the outside via a wireless method.

The X-ray imaging apparatus may further include a stopper configured to fasten the first plate with respect to the base in the first and second states.

The X-ray imaging apparatus may further include a fastener configured to detachably fasten the X-ray detecting device on the first plate.

The X-ray imaging apparatus may further include a plurality of location guides, some of which are configured to guide a location of the X-ray detecting device such that a center of the bucky tray matches a center of the X-ray detecting device.

The X-ray imaging apparatus may further include a second plate coupled to the first plate to be able to move to a first location where the X-ray detecting device of a first size is accommodated and to a second location where the X-ray detecting device of a second size is accommodated.

The second plate may be configured to slide with respect to the first plate to the first and second locations.

The first plate and the second plate may be configured to symmetrically slide in directions opposite the first and second locations.

The X-ray imaging apparatus may further include a slide fastener configured to fasten the second plate in the first and second locations.

The X-ray detecting device may include a first terminal and the second plate may include a second terminal connected to the first terminal.

The X-ray imaging apparatus may further include a plurality of location guides configured to guide a location of the X-ray detecting device such that a center of the bucky tray matches a center of the X-ray detecting device, and at least one of the plurality of location guides may be provided on the second plate.

The plurality of location guides may be configured to be movable on the base.

A size of the X-ray detecting device may be 8×10 inches, 10×12 inches, 14×14 inches, 14×17 inches, or 17×17 inches.

The X-ray imaging apparatus may further include a controller configured to receive from the rotation sensor or the detachment sensor a sensing signal indicating whether the X-ray detecting device is detached from the bucky tray or indicating an arrangement location of the X-ray detecting device and transmit a control signal regarding an X-ray exposure area to an X-ray emitter.

BRIEF DESCRIPTION OF THE DRAWINGS

The above and/or other aspects will become more apparent by describing certain exemplary embodiments with reference to the accompanying drawings, in which.

DETAILED DESCRIPTION

Figure 1:
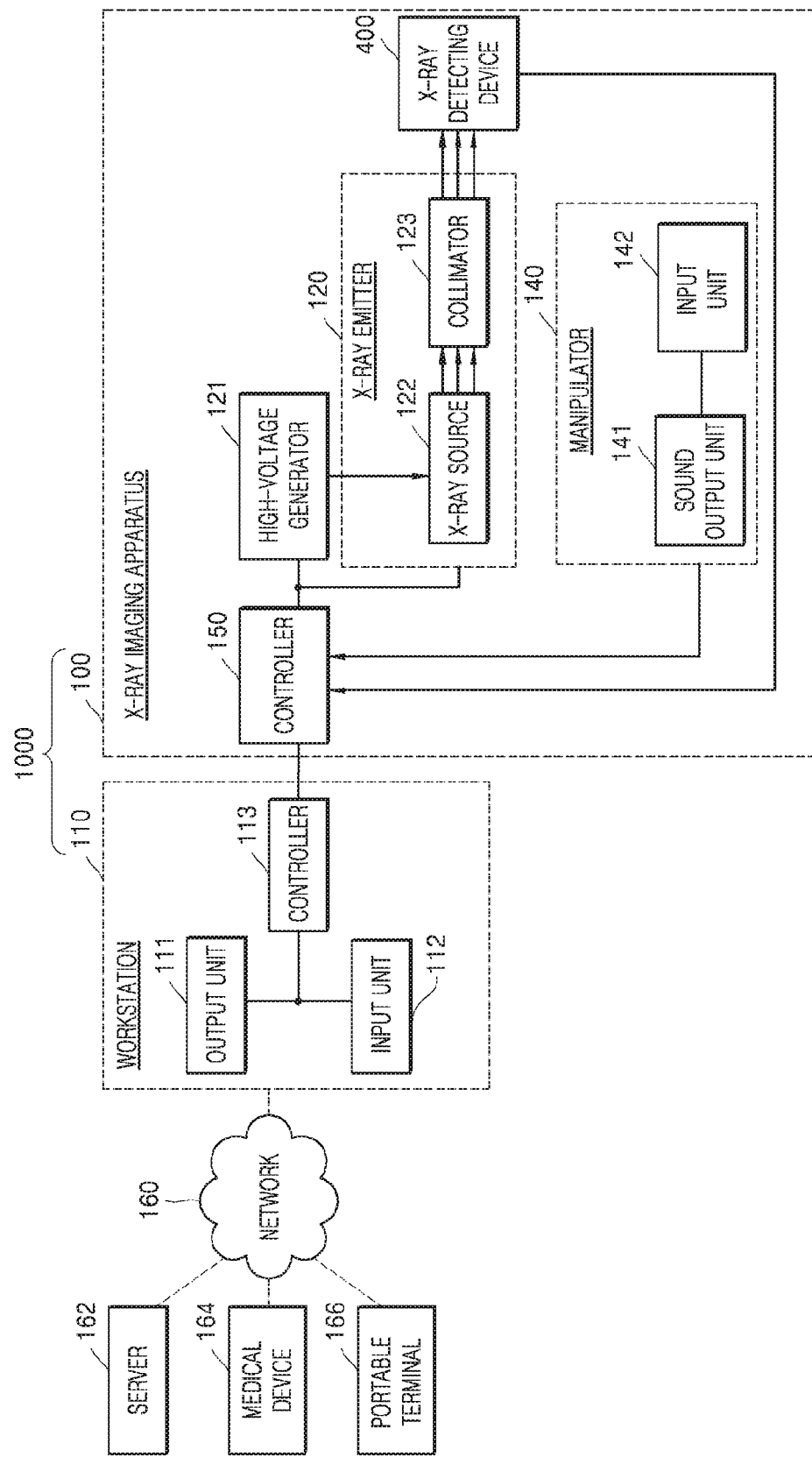
FIG. 1 is a block diagram of a structure of an X-ray imaging apparatus according to an exemplary embodiment.

Certain exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments may be practiced without those specifically defined matters. Also, well-known functions or constructions are not described in detail since they would obscure the description with unnecessary detail.

Throughout the specification, an "image" may refer to multi-dimensional data formed of discrete image elements, for example, pixels in a two-dimensional (2D) image and voxels in a three-dimensional (3D) image. Examples of the "image" may include a medical image of an object, etc., obtained by an X-ray apparatus, a computed tomography (CT) apparatus, a magnetic resonance imaging (MRI) apparatus, an ultrasound apparatus, and other medical imaging apparatuses.

In addition, in the present specification, an "object" may include a person or an animal, or a part of a person or an animal. For example, the object may include at least one of the liver, the heart, the womb, the brain, a breast, the abdomen, and a blood vessel. Furthermore, the "object" may include a phantom. The phantom means a material having a volume that is approximately the intensity and effective atomic number of a living thing, and may include a sphere phantom having a property similar to a human body.

Furthermore, in the present specification, a "user" may refer to a medical professional, such as a doctor, a nurse, a medical laboratory technologist, and an engineer who repairs a medical apparatus, but the user is not limited thereto.

FIG. 1 is a block diagram of a structure of an X-ray apparatus 1000 which includes an X-ray imaging apparatus 100 according to an exemplary embodiment. The X-ray imaging apparatus 100 illustrated in FIG. 1 may be a fixed-type X-ray imaging apparatus or a mobile X-ray imaging apparatus.

Referring to FIG. 1, the X-ray imaging apparatus 100 may include an X-ray emitter 120, a high-voltage generator 121, and an X-ray detecting device 400. As a non-limiting example, the X-ray detecting device may have a detection area equal to or greater than 14×17 inches and a matrix of more than 2000 pixels in a horizontal axis and more than 2000 pixels in a vertical axis, the length of pixels being equal to or smaller than 200 µm.

The workstation 110 includes an input unit 112 and an output unit 111 configured to input or output commands of a user to manipulate the X-ray imaging apparatus 100, the commands including, for example, a command to emit X-rays. The input unit 112 may include at least one of a switch, a keyboard, a mouse, a touch screen, a voice recognizer, a fingerprint recognizer, an iris recognizer, and other input devices which are known to one of ordinary skill in the art. A controller 113 is configured to control operations of the X-ray imaging apparatus 100.

The high-voltage generator 121 generates high voltages for generating X-rays and applies the generated high voltages to an X-ray source 122.

The X-ray emitter 120 includes the X-ray source 122 configured to receive the high voltages generated by the high-voltage generator 121 to generate and emit X-rays, and a collimator 123 configured to guide a path of the X-rays emitted by the X-ray source 122.

The X-ray detecting device 400 detects the X-rays that were emitted by the X-ray emitter 120 and have penetrated an object.

The X-ray imaging apparatus 100 may further include a manipulator 140 which includes an input unit 142 and a sound output unit 141 configured to output a sound indicating imaging-related information, such as an emission of X-rays, according to a control of the controller 113. The input unit 142 may include any of the input devices described above with reference to the input unit 112.

The workstation 110, the X-ray emitter 120, the high-voltage generator 121, and the X-ray detecting device 400 may be connected with one another by wires or wirelessly, and when the workstation 110, the X-ray emitter 120, the high-voltage generator 121, and the X-ray detecting device 400 are connected wirelessly, the X-ray imaging apparatus 100 may further include a device (not shown) for synchronizing clocks among one another.

A user may input a command for emitting X-rays via the input unit 112. The input unit 112 may include a switch via which such a command is input. The switch may operate in a way in which the command for emitting X-rays is input, when the switch is pressed two times.

For example, when a user presses the switch once, a prepare command for initiation of the preheating of the high-voltage generator 121 for X-ray emission is input, and when, in this state, the user presses the switch one more time, an emission command for an X-ray emission is input. When the user operates the switch in this manner, the input unit 112 generates signals corresponding to a preparation signal and an emission signal, and the input unit 112 outputs the signals to the high-voltage generator 121 for generating high-voltages for an X-ray emission.

When the high-voltage generator 121 receives the preparation signal from the input unit 112, the high-voltage generator 121 starts preheating, and when the preheating is completed, the high-voltage generator 121 outputs a preparation completion signal to the controller 113. Further, the X-ray detecting device 400 needs a preparation for the X-ray detection. When the high-voltage generator 121 receives the preparation signal from the input unit 112, the high-voltage generator 121 outputs a preparation signal to the X-ray detecting device 400 so that the X-ray detecting device 400 starts preparing for detecting X-rays, while the high-voltage generator 121 preheats. When the preparation for the X-ray detection is completed, the X-ray detecting device 400 outputs a signal of a preparation completion to the high-voltage generator 121 and/or the controller 113.

When the preheating of the high-voltage generator 121 and the preparation of the X-ray detecting device 400 for the X-ray detection are completed, and the emission signal of the input unit 112 is output to the high-voltage generator 121, the high-voltage generator 121 generates high voltages and applies the high voltages to the X-ray source 122, and the X-ray source 122 emits X-rays.

When the emission signal is output from the input unit 112, the controller 113 may output a sound output signal to the sound output unit 141 to output a predetermined sound, so that the X-ray emission is informed to the object. The sound output unit 141 may output a sound which indicates the imaging-related information other than the X-ray emission. Although FIG. 1 illustrates that the sound output unit 141 is included in the manipulator 140, it is not limited thereto, and the sound output unit 141 may be located separately from the manipulator 140. For example, the sound output unit 141 may be included in the workstation 110, or may be located on a wall of a room where X-ray imaging for an object is performed.

The controller 113 controls locations of the X-ray emitter 120 and the X-ray detecting device 400, and imaging timings and conditions, according to imaging conditions which are configured by a user.

In detail, the controller 113 controls a timing for an X-ray emission, an intensity of X-rays, an area of the X-ray emission, etc., by controlling the high-voltage generator 121 and the X-ray detecting device 400 according to commands that are input via the input unit 112. The controller 113 adjusts a location of the X-ray detecting device 400 and controls an operation timing of the X-ray detecting device 400, based on predetermined imaging conditions.

The controller 113 generates a medical image of the object by using image data received from the X-ray detecting device 400. In detail, the controller 113 may receive the image data from the X-ray detecting device 400, remove noises of the image data, and generate the medical image of the object by adjusting a dynamic range and interleaving.

The X-ray imaging apparatus 100 of FIG. 1 may further include an output unit 111 configured to output the medical image generated by the controller 113. The output unit may output a user interface (UI), user information, or object information needed for a user to manipulate the X-ray imaging apparatus 100. The output unit may include at least one of a printer, a cathode ray tube (CRT) display, a liquid-crystal display (LCD), a plasma display panel (PDP) display, an organic light-emitting diode (OLED) display, a field emission display (FED), a light-emitting device (LED) display, a vacuum fluorescent display (VFD), a digital light processing (DLP) display, a flat panel display (FPD), a 3D display, a transparent display, and other appropriate output devices which are known to one of ordinary skill in the art. Although the output unit 111 is shown incorporated into the workstation 110, this is not limiting and the output unit 111 may be disposed separately from the workstation 110.

The workstation 110 may further include a communicator (not shown) which may be connected to the network 160 by wires or wirelessly to perform communication with the external server 162, the external medical device 164, or the external portable terminal 166. The communicator may exchange data related to a diagnosis of an object, and a medical image imaged by other medical device 164, such as a CT, an MRI, or another X-ray imaging apparatus, with the external server 162, the external medical device 164, or the external portable terminal 166, via the network 160. Further, the communicator may receive a diagnostic record or a treatment schedule of a patient from the server 162 and use the received information for making a diagnosis for the object. The communicator may perform data communication not only with the server 162 or the medical device 164 within a hospital, but also with the portable terminal 166, such as a cellular phone, a personal digital assistant (PDA), and a notebook of a doctor or a patient.

The communicator may include one or more components which make possible communication with external devices. For example, the communicator may include a near-field communication module, a wired communication module, and a wireless communication module.

The near-field communication module refers to a module for performing near-field communication with a device located within a predetermined distance. The near-field communication technology according to an exemplary embodiment may include a wireless local area network (LAN), Wi-fi, Bluetooth, ZigBee, Wi-fi direct (WFD), ultra wideband (UWB), infrared data association (IrDA), Bluetooth low energy (BLE), near-field communication (NFC), etc. However, the near-field communication technology is not limited thereto.

The wired communication module refers to a module for communication performed by using electrical signals or optical signals. The wired communication technology may include wired communication technologies using a pair cable, a coaxial cable, an optical fiber cable, etc., and other wired communication technologies that are known to one of ordinary skill in the art.

The wireless communication module exchange a wireless signal with at least one of a base station in a mobile communication network, an external device, and an external server. The wireless signal may include a voice call signal, a video call signal, or various types of data according to an exchange of a text/multimedia messages.

The X-ray imaging apparatus 100 illustrated in FIG. 1 may include a plurality of digital signal processing devices (DSP), subminiature operation processing devices, and application-specific (for example, high speed analog to digital (A/D) conversion, high speed Fourier transformation, array processing, etc.) processing circuits.

The communication between the workstation 110 and the X-ray emitter 120, between the workstation 110 and the high-voltage generator 121, and between the workstation 110 and the X-ray detecting device 400 may be performed by using a high speed digital interface, such as low voltage differential signaling (LVDS), asynchronous serial communication, such as a universal asynchronous receiver transmitter (UART), a low latency network protocol, such as synchronous serial communication or a controller area network (CAN), and other various communication methods known to one skilled in the art.

Figure 2:
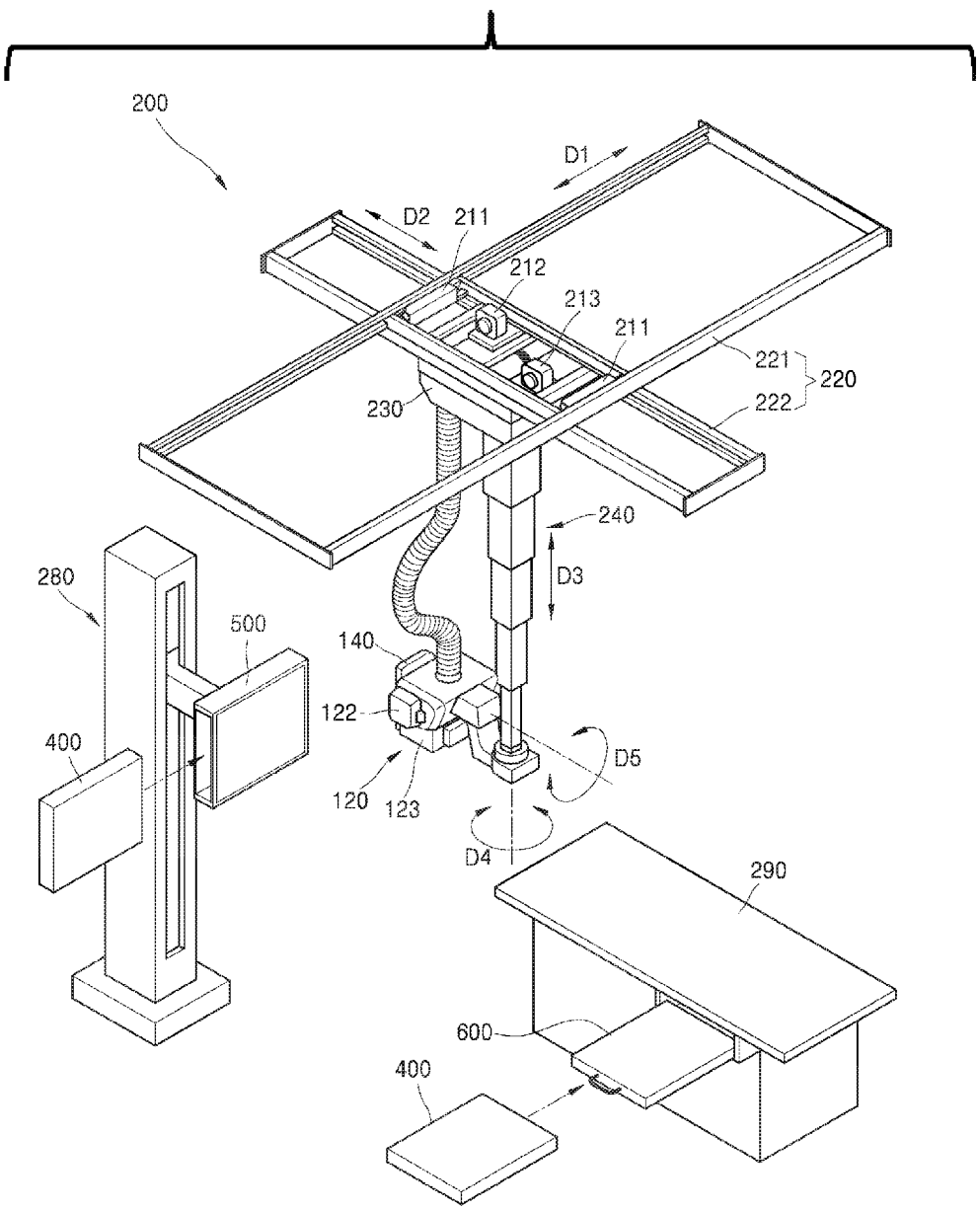
FIG. 2 is a perspective view of a fixed-type X-ray imaging apparatus according to an exemplary embodiment.

FIG. 2 is a perspective view of a fixed-type X-ray imaging apparatus 200 according to an exemplary embodiment.

As illustrated in FIG. 2, the X-ray imaging apparatus 200 includes the manipulator 140 configured to provide an interface for the manipulation of the X-ray imaging apparatus 200, the X-ray emitter 120 configured to emit X-rays to an object, the X-ray detecting device 400 configured to detect the X-rays which have penetrated the object, motors 211, 212, and 213 configured to provide a driving force to move the X-ray emitter 120, a guide rail 220 configured to move the X-ray emitter 120 by using the driving force provided by the motors 211, 212, and 213, a moving carriage 230, and a post frame 240.

The guide rail 220 includes a first guide rail 221 and a second guide rail 222 which are arranged to form a predetermined angle. For example, the first guide rail 221 and the second guide rail 222 may extend in a direction in which the first guide rail 221 and the second guide rail 222 cross each other at right angles.

The first guide rail 221 is provided in a ceiling of an examination room where the X-ray imaging apparatus 200 is arranged.

The second guide rail 222 is located below the first guide rail 221, and is mounted to be slidable relative to the first guide rail 221. A roller (not shown) which is capable of moving along the first guide rail 221 may be mounted in the first guide rail 221. The second guide rail 222 may be connected to the roller and may move along the first guide rail 221.

A direction in which the first guide rail 221 extends is defined as a first direction D1, and a direction in which the second guide rail 222 extends is defined as a second direction D2. Thus, the first direction D1 and the second direction D2 may cross each other at right angles and may be parallel to the ceiling of the examination room.

The moving carriage 230 is arranged below the second guide rail 222 to be able to move along the second guide rail 222. A roller (not shown) by which the moving carriage 230 may move along the second guide rail 222 may be provided in the moving carriage 230.

Accordingly, the moving carriage 230 is able to move in the first direction D1 together with the first guide rail 221, and in the second direction D2 along the second guide rail 222.

The post frame 240 is arranged below the moving carriage 230 by being fastened to the moving carriage 230. The post frame 240 may include a plurality of posts. The plurality of posts are connected such that the plurality of posts may be folded with one another, so that the post frame 240 may have an increased or a decreased length in an up and down direction of the examination room, while being fastened to the moving carriage 230.

A direction in which the length of the post frame 240 is increased or decreased is defined as a third direction D3 which may cross the first direction D1 and the second direction D2 at right angles.

The motors 211, 212, and 213 may be provided to move the X-ray emitter 120 in the first direction D1 through the third direction D3. The motors 211, 212, and 213 may be motors that are electrically driven, and at least one of the motors 211, 212, and 213 may include an encoder.

The motors 211, 212, and 213 may be arranged in any positions for convenience of design. For example, the first motor 211 which moves the second guide rail 222 in the first direction D1 may be arranged around the first guide rail 221, the second motor 212 which moves the moving carriage 230 in the second direction D2 may be arranged around the second guide rail 222, and the third motor 213 which increases or decreases the length of the post frame 240 in the third direction D3 may be arranged inside the moving carriage 230. As another example, the motors 211, 212, and 213 may be connected to a driving force transmitter (not shown) to linearly move the X-ray emitter 120 in the first direction D1 through the third direction D3. The driving force transmitter may include at least one of a belt, a pulley, chains, sprockets, a shaft, etc.

The X-ray source 122 may include an X-ray tube including a two electrode vacuum tube including a positive electrode and a negative electrode. The X-ray tube is made into a high vacuum state of about 10 mmHg, and a filament of the negative electrode is heated to a high temperature to generate thermoelectrons. The filament may include a tungsten filament, which may be heated by applying a voltage of about 10V and a current of about 3-5 mA to electric wires connected to the filament.

Then, when a high voltage of about 10-300 kVp is applied between the negative electrode and the positive electrode, the thermoelectrons are accelerated and collide with a target material of the positive electrode, in order to generate X-rays. The generated X-rays are emitted to the outside via a window. The window may be formed of a barium thin film. Here, most of energy of the electrons colliding with the target material is consumed as heat, and the rest portion of the energy which remains thereafter is converted into X-rays.

The positive electrode may be mainly formed of copper, and the target material may be disposed to face the negative electrode. The target material may include high-resistance materials, such as Cr, Fe, Co, Ni, W, Mo, etc. The target material may rotate by a rotating field, and when the target material rotates, an electron shock area may be increased, and a thermal build up rate may be increased by more than 10 times per unit area, compared with the case where the target material is fixed.

The voltage applied between the negative electrode and the positive electrode of the X-ray tube, i.e., a tube voltage, may be applied from the high-voltage generator 121 and a magnitude thereof may be indicated as kVp. When the tube voltage is increased, a speed of the thermoelectrons is increased, and thus, the energy of the X-rays (energy of a photon), which are generated when the thermoelectrons collide with the target material, is increased. A current flowing in the X-ray tube, i.e., a tube current, may be indicated as an average value (mA). When the tube current is increased, the number of thermoelectrons emitted from the filament is increased, and thus, a dose of the X-rays (the number of photons of the X-rays), which are generated when the thermoelectrons collide with the target material, is increased.

Thus, the energy of the X-rays may be controlled by the tube voltage, and the intensity or the dose of the X-rays may be controlled by the tube current and an X-ray exposure time.

The high-voltage generator 121 may be provided in the X-ray source 122, but it is not limited thereto. The high-voltage generator 121 may be provided in other positions in the X-ray imaging apparatus 200.

The manipulator 140 which provides the interface by which various types of information related to X-ray imaging are input and various devices are manipulated, is provided on a side surface of the X-ray emitter 120.

FIG. 2 illustrates the fixed-type X-ray imaging apparatus 200 which is connected to the ceiling of the examination room. However, it is only an example. The X-ray imaging apparatus according to exemplary embodiments may include various types of X-ray imaging apparatuses which are known to one of ordinary skill in the art, such as a C-arm X-ray imaging apparatus, an angiography X-ray imaging apparatus, etc.

The X-ray detecting device 400 may detect the X-rays that have penetrated the object, and may be associated with a table 290 or a stand 280.

Figure 3:
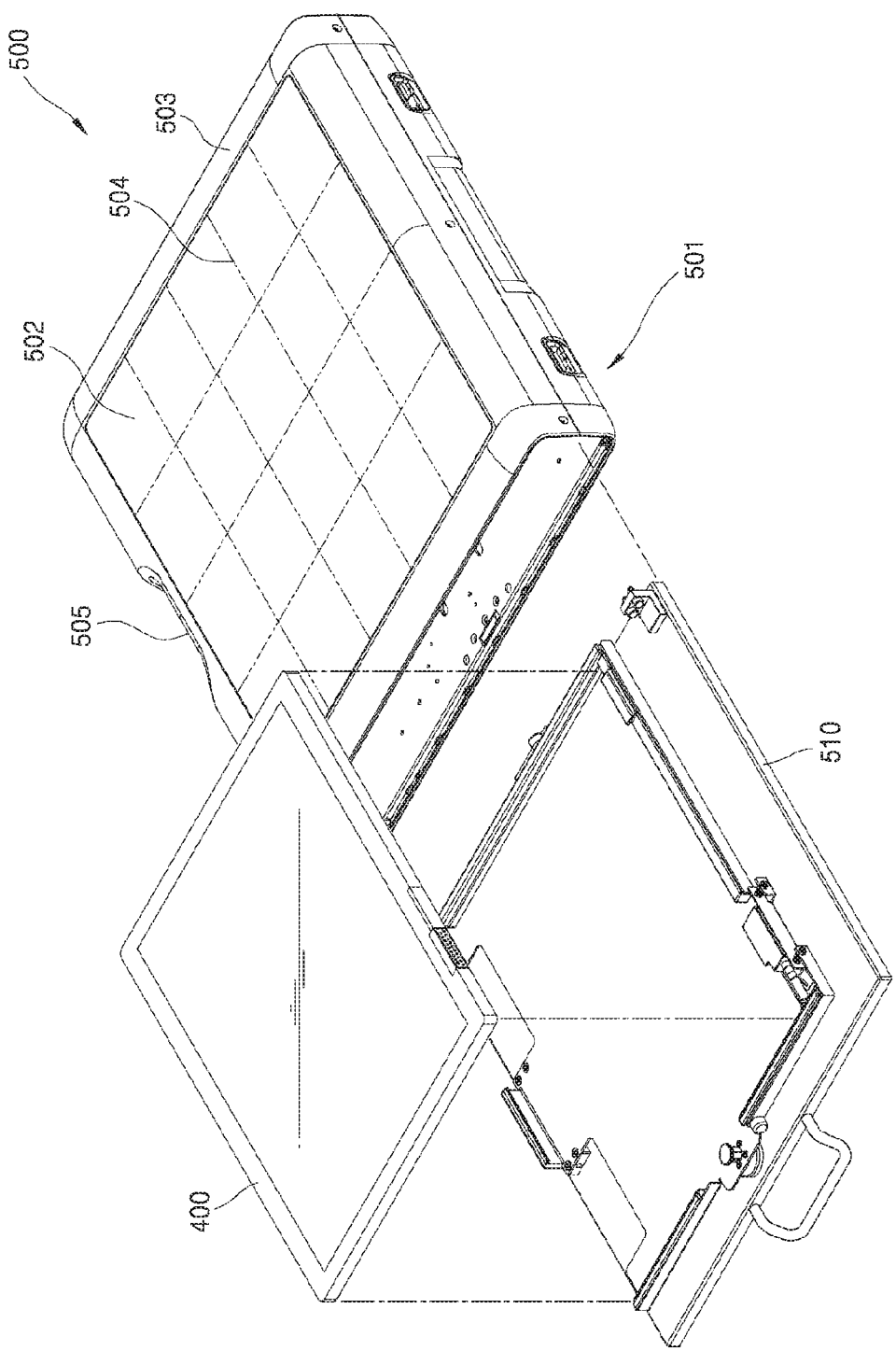
FIG. 3 is a perspective view of a stand-type bucky according to an exemplary embodiment.

FIG. 3 is a perspective view of a stand-type bucky 500 according to an exemplary embodiment.

Referring to FIG. 3, the X-ray detecting device 400 may be accommodated in the stand-type bucky 500. The related art analog X-ray detecting device uses a film plate combining an intensifying screen (a fluorescent plate) which emits light when X-rays are applied thereto and a silver salt film, wherein the film plate has to be repeatedly mounted and detached whenever examinations are performed. The digital X-ray detecting device 400 obtains image data by digital signals by using computer radiography (CR) using an image plate, a charge-coupled device (CCD) detector using a scintillator and a charge-coupled device, and a flat panel detector using a thin film transistor, and thus, the digital X-ray detecting device 400 may obtain a desired image without repeatedly detaching and mounting the film plate whenever the examinations are performed. However, since an arrangement and a size of the X-ray detecting device 400 may vary according to use of the X-ray detecting device 400, the stand-type bucky 500 for accommodating the X-ray detecting device 400 needs to be formed to be able to easily accommodate the X-ray detecting devices 400 of various sizes, at various angles.

The stand-type bucky 500 may include a bucky tray 510 via which the X-ray detecting device 400 is detached and attached, and an accommodation unit 501 in which the X-ray detecting device 400 is accommodated. The accommodation unit 501 accommodates the X-ray detecting device 400, and may include an incident surface 502, a chamber 503, and an object support 505. The incident surface 502 is a plate member arranged to face the X-ray emitter 120, and is formed of ebonite, etc., on which the X-rays incident. An anti-scattered grid 504 may be arranged in parallel to the incident surface 502, at a backward portion of the incident surface 502. When an anti-scattered grid is arranged, scattered rays which may be generated when X-rays penetrate an object may be removed, so that an image quality of the detecting device may be improved. The chamber 503 may be formed of a metal, such as aluminum, Bakelite, etc., and may accommodate the X-ray detecting device 400. The chamber 503 may include an ion-chamber inside thereof to measure an amount of X-rays which have penetrated an object. The object support 505 may be a supporting area via which an object 10 (refer to FIG. 8) is supported in the stand-type bucky 500, when a diagnostics is performed with respect to the object. For example, the object support 505 may have a convex member formed therein to conform to and support the chin of the object 10.

Figure 4A:
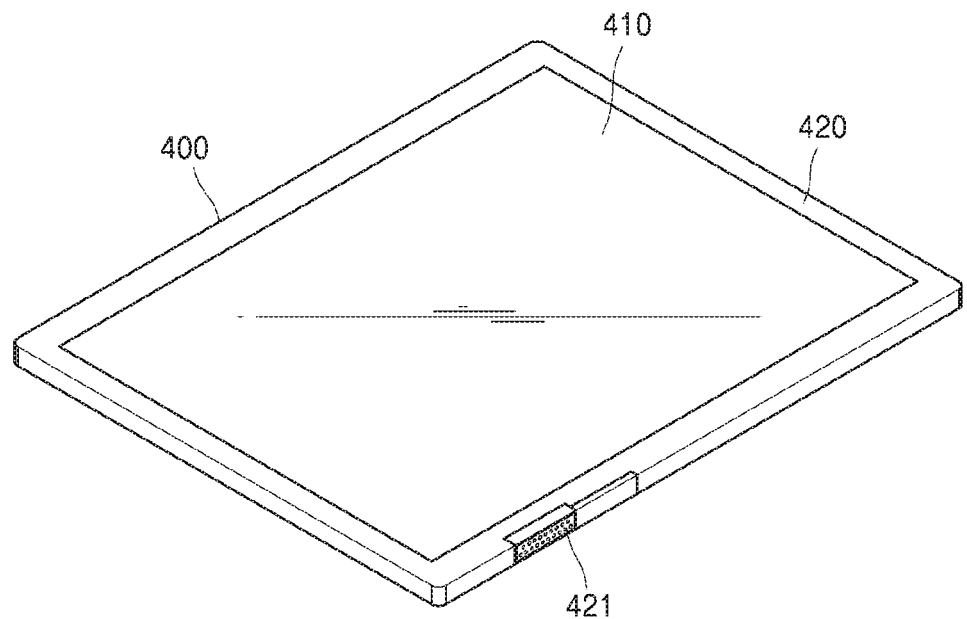
FIG. 4A is a perspective view of an X-ray imaging apparatus according to an exemplary embodiment.
Figure 4B:
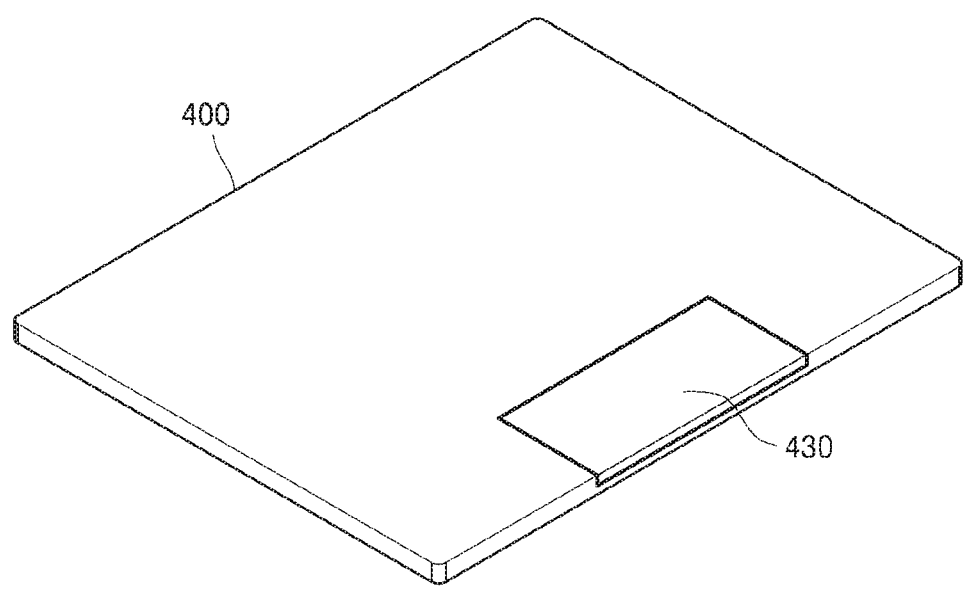
FIG. 4B is a rear view of the X-ray imaging apparatus of FIG. 4A.
Figure 4C:
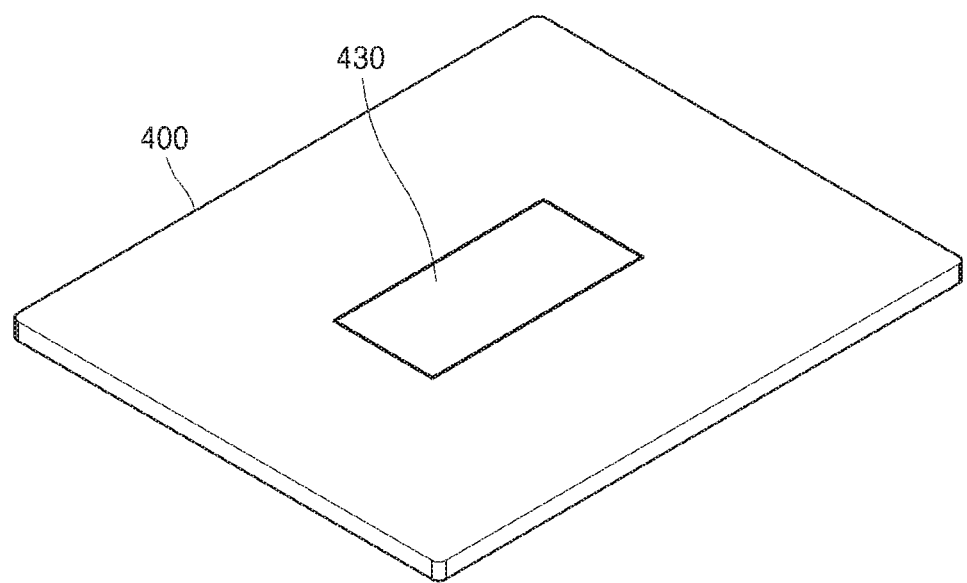
FIG. 4C is a rear view of the X-ray imaging apparatus of FIG. 4A.

FIG. 4A is a perspective view of the X-ray detecting device 400 according to an exemplary embodiment. FIGS. 4B and 4C are rear views of the X-ray detecting device 400 of FIG. 4A.

Referring to FIG. 4A, the X-ray detecting device 400 may include a sensor 410 which is a detecting medium responsive to X-rays and includes a 2D sensor, and a sensor case 420 which accommodates the sensor 410. The sensor 410 is arranged to face the X-ray emitter 120, and when the X-rays emitted from the X-ray emitter 120 are applied to the sensor 410, the sensor 410 obtains electrical signals generated in the 2D sensor. The electrical signals obtained by the 2D matrix are converted into digital values to form image data, which is displayed on a monitor or a printer after undergoing through an appropriate imaging process.

The sensor case 420 may include various sizes, for example, at least one of 8×10 inches, 10×12 inches, 14×14 inches, 14×17 inches, and 17×17 inches, based on a size of the sensor 410, i.e., such as 8×10 inches, 10×12 inches, 14×14 inches, 14×17 inches, and 17×17 inches.

The sensor case 420 may include a first terminal 421 which includes a power terminal, e.g., a pin or a socket, which receives power from the outside or supplies power to a battery disposed inside the sensor case 420, and a signal terminal, e.g., a pin or a socket, which transmits the electrical signals obtained from the sensor 410 to the outside. In the present exemplary embodiment, the first terminal 421 is disposed on a side portion of the sensor case 420. However, this is not limiting. The first terminal 421 may be arranged on a rear portion of the sensor case 420, or may be arranged such that the first terminal 421 receives power and transmits signals wirelessly.

The X-ray detecting device 400 may be formed as a mobile device and may include a battery 430, e.g., an auxiliary battery.

Referring to FIGS. 4B and 4C, the battery 430 may be arranged at a side portion or a central portion of the X-ray detecting device 400. The battery 430 may be a separate battery which can be separated from the X-ray detecting device 400 or an integral type which is integrated with the X-ray detecting device 400. The battery 430 may be charged outside, while being separated from the X-ray detecting device 400, or may be charged by wires via the first terminal 421. Alternatively, the battery 430 may be charged wirelessly.

Figure 5A:
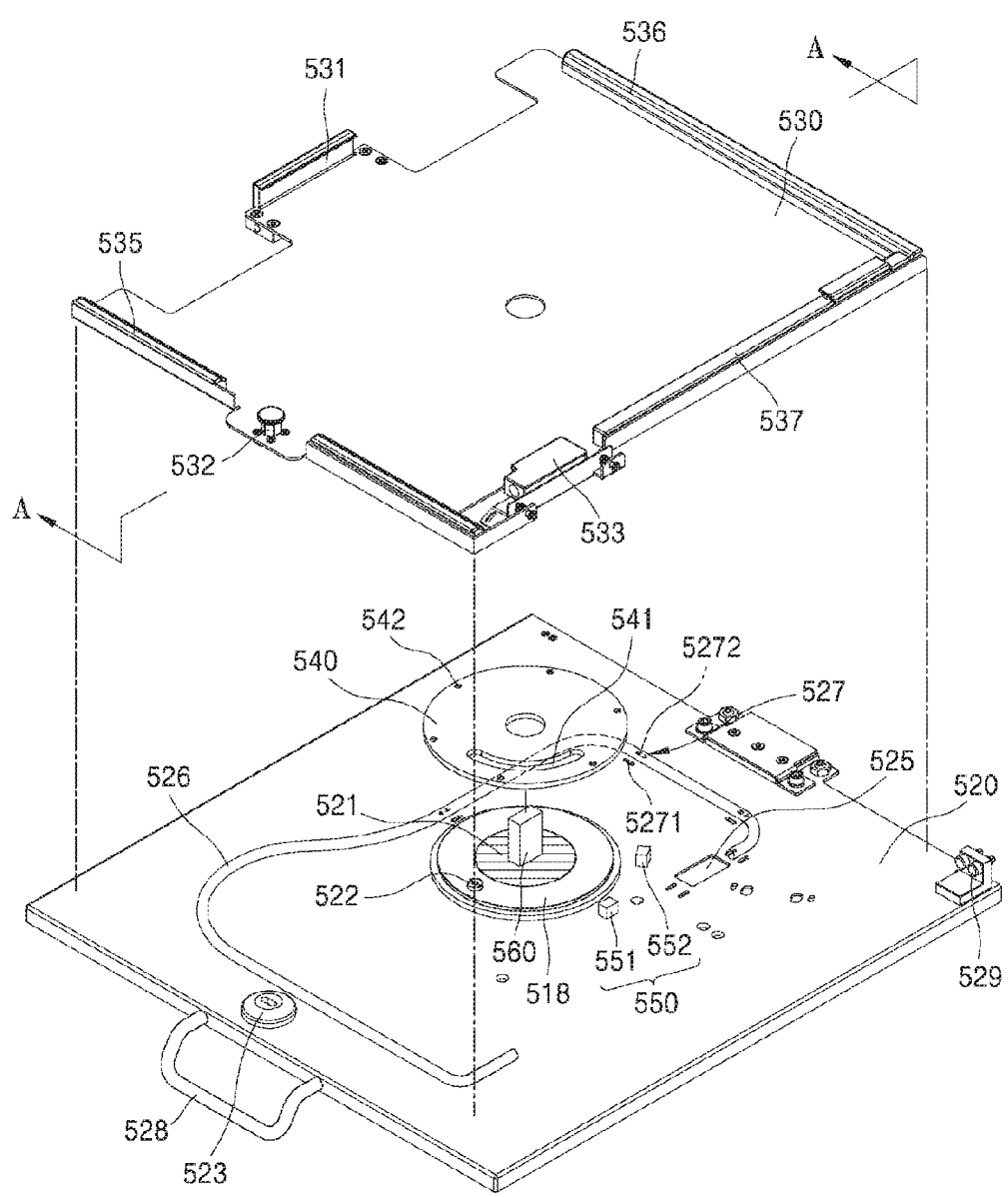
FIG. 5A is an exploded perspective view of a bucky tray according to an exemplary embodiment.
Figure 5B:
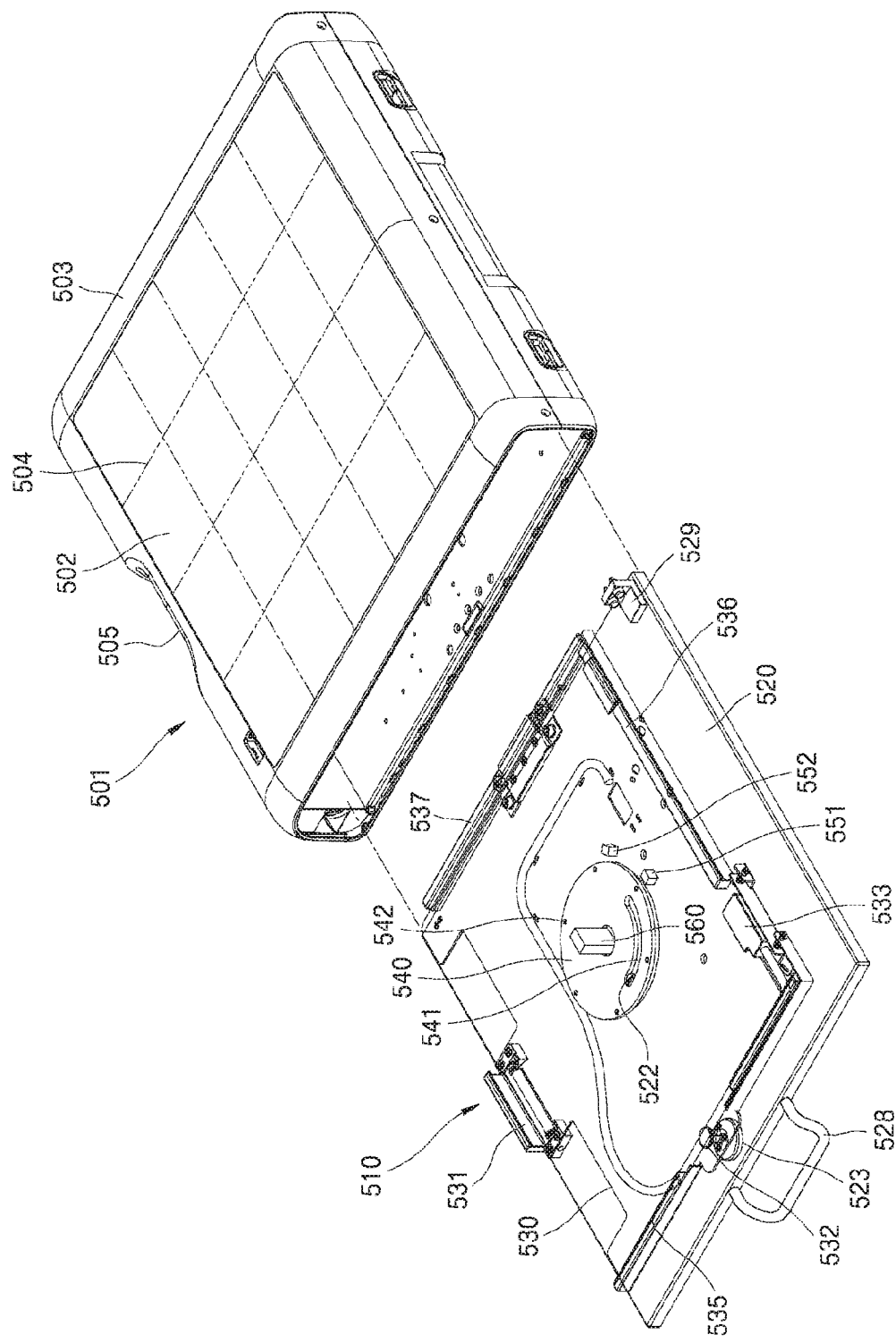
FIG. 5B is a perspective view of a stand-type bucky according to an exemplary embodiment.
Figure 5C:
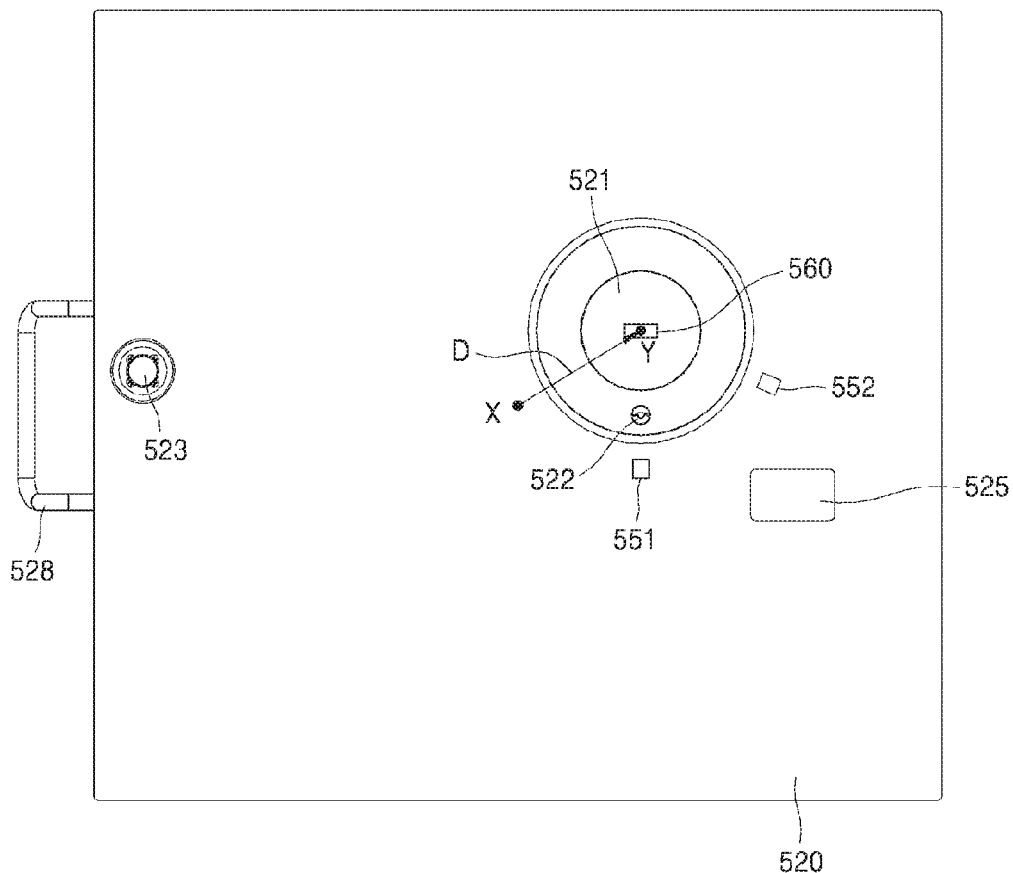
FIG. 5C is a plan view of a base of FIG. 5A.
Figure 5D:
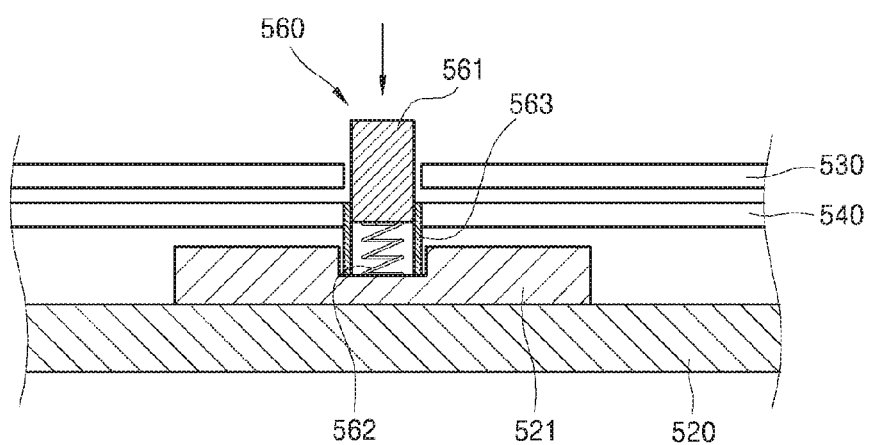
FIG. 5D is a cross-sectional view taken along line A-A of the bucky tray of FIG. 5A.
Figure 5E:
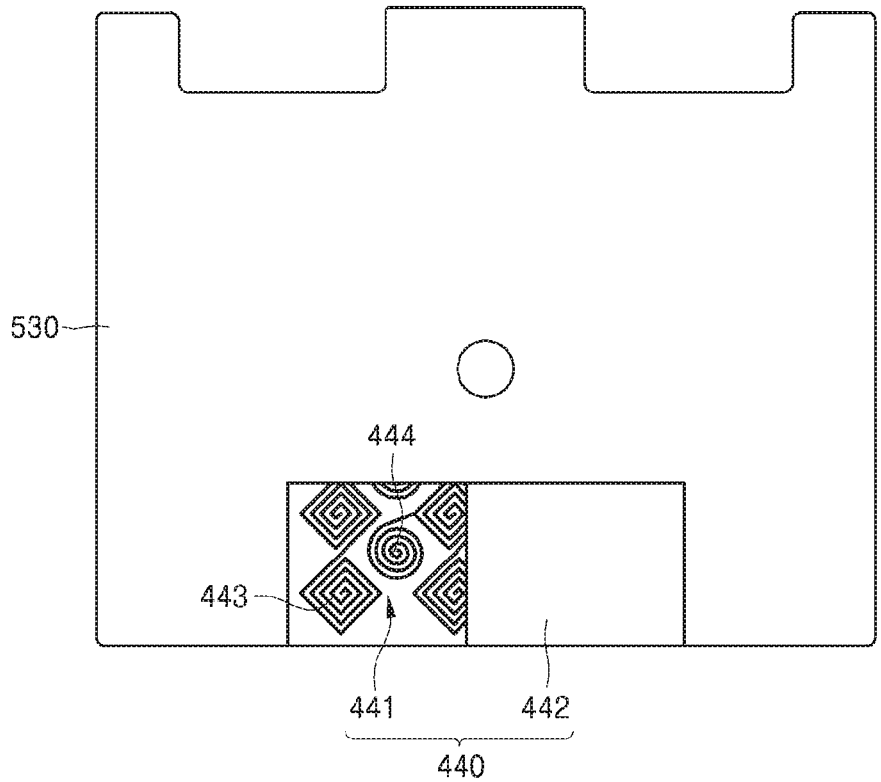
FIG. 5E is a rear view of a first plate of FIG. 5A.
Figure 5F:
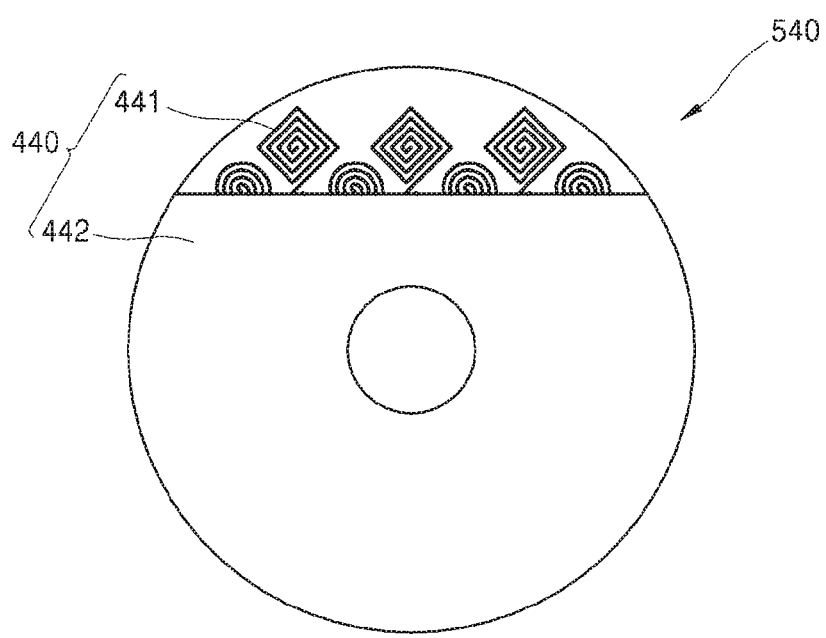
FIG. 5F is a rear view of a rotation plate of FIG. 5A.

FIG. 5A is an exploded perspective view of the bucky tray 510 according to an exemplary embodiment, and FIG. 5B is a perspective view of the stand-type bucky 500 according to an exemplary embodiment. FIG. 5C is a plan view of a base 520 illustrated in FIG. 5A, and FIG. 5D is a cross-sectional view taken along line A-A of the bucky tray 510 of FIG. 5A. FIG. 5E is a rear view of a first plate 530 illustrated in FIGS. 5A, and 5F is a rear view of a rotation plate 540 illustrated in FIG. 5A.

Referring to FIGS. 5A and 5B, the bucky tray 510 may include the base 520 which may be accommodated in and discharged from the accommodation unit 501, and the first plate 530 which is arranged on the base 520 to be rotatable. The base 520 is a plate member, i.e., has a plate-like shape with two flat surfaces facing each other on front and rear sides. On a front surface of the base 520, a central member 521 of a cylindrical shape 518 extending in a X-ray emission direction, a first guide 522, a first stopper 523 formed at a side portion of the base 520, a penetration hole 525 through which a detector cable 526 of the X-ray detecting device 400 may penetrate, the detector cable 526 which is connected to a second terminal 533 to transmit an electrical signal detected from the X-ray detecting device 400 to the outside, and a plurality of cable fasteners 527 for preventing twists of the detector cable 526 are provided. A handle 528 of a link shape may be disposed at a side portion of the base 520, and the bucky tray 510 may be easily accommodated in and discharged from the accommodation unit 501 by using the handle 528.

Referring to FIG. 5C, a center Y of the central member 521 may be eccentric from a center X of the base 520 in a direction D. Accordingly, even if the X-ray detecting device 400 rotates against the base 520 in the stand-type bucky 500, the X-ray detecting device 400 may maintain a diagnostic location of the object 10.

The first plate 530 is a plate member on which the X-ray detecting device 400 is mounted. The first plate 530 is disposed to be rotatable with respect to the base 520. On a surface of the first plate 530 on which the X-ray detecting device 400 is disposed, a first fastener 531 configured to fasten the X-ray detecting device 400, a second stopper 532 which is coupled to the first stopper 523 of the base 520 to prevent a rotation of the first plate 530, the second terminal 533 which may be connected to the first terminal 421 of the X-ray detecting device 400, and a plurality of location guides 535, 536, and 537 configured to adjust a location of the X-ray detecting device 400 are disposed, along a side portion of the first plate 530.

The first fastener 531 is disposed at a side portion of the first plate 530 to be rotatable by using a hinge structure, in order to fasten the X-ray detecting device 400. A twist elastic member (not shown) may be disposed at both ends of the hinge unit of the first fastener 531. When a side portion of the sensor case 420 is inserted between the first fastener 531 and the first plate 530, the first fastener 531 may rotate in a counter clockwise direction so that X-ray detecting device 400 is fastened to the first plate 530. When the X-ray detecting device 400 is released from the first plate 530, the first fastener 531 may rotate in a clockwise direction by a restoring force by the twist elastic member, and may be restored to an original position thereof.

In the present exemplary embodiment, the X-ray detecting device 400 is fastened to the first plate 530 by using the first fastener 531 and the elastic member. However, an exemplary embodiment is not limited thereto. Other types of fastening members which may fasten the X-ray detecting device 400 to the first plate 530, for example, a screw clamping structure, etc., may be adapted.

In the stand-type bucky 500, the first plate 530 which is disposed at a diagnostic location to be rotatable with respect to the base 520 may rotate by itself with respect to the base 520 due to weights of the X-ray detecting device 400 and the first plate 530, and thus, a fastening device which may prevent this rotation may be needed. The second stopper 532 may prevent the rotation of the first plate 530 with respect to the base 520, by being coupled to the first stopper 523 provided in the base 520. The second stopper 532 may have, for example, a bar-shape which can be inserted into the first stopper 523 provided as a shape of a penetration hole, and the first plate 530 may be fastened to the base 520 to restrict the rotation of the first plate 530 in the counter clockwise direction with respect to the base 520. A third stopper, for example, a stopping protrusion 529 provided as a permanent magnet may be disposed at another side portion which is adjacent to the side portion of the base 520 at which the first stopper 523 is disposed, in order to restrict the rotation of the first plate 530 in the clockwise direction with respect to the base 520.

The second terminal 533 may be disposed to be fastened to a side portion of the first plate 530, and even if the first plate 530 rotates with respect to the base 520, the second terminal 533 may be connected to the first terminal 421 of the X-ray detecting device 400 at the same location. However, an exemplary embodiment is not limited thereto, and when the first terminal 421 of the X-ray detecting device 400 is a wireless terminal, the second terminal 533 of the first plate 530, which interacts with the first terminal 421, may also be a wireless terminal, and thus, locations of the X-ray detecting device 400 and the terminal disposed on the first plate 530 are not restricted.

The detector cable 526 may be disposed between the base 520 and the first plate 530, in a state in which an end thereof is connected to the second terminal 533. The other end of the detector cable 526 extends to a rear surface of the base 520 via the penetration hole 525 provided in the base 520, to be connected to the outside. An electrical signal generated by the X-ray detecting device 400 may be transmitted to the outside by using the detector cable 526. Since an end of the detector cable 526 is connected to the second terminal 533 and the other end of the detector cable 526 is connected to the outside, a twist may occur in the detector cable 526 when the first plate 530 rotates.

The plurality of cable fasteners 527 may be disposed on the base 520 with a predetermined distance therebetween, to adjust a location of the detector cable 526 and prevent the twist of the detector cable 526. A first cable fastener 5271 and a second cable fastener 5272 are disposed on the base 520 to be apart from each other by a distance which is greater than a diameter of the detector cable 526, and the detector cable 526 is disposed between the first cable fastener(s) 5271 and the second cable fastener(s) 5272 to slide while being restricted in-between the first cable fasteners 5271 and the second cable fasteners 5272. Thus, even if the first plate 530 rotates, twists of the detector cable 526 may be prevented since the detector cable 526 may slide along a path in which the plurality of cable fasteners 527 are arranged, at various locations along the path.

In the present exemplary embodiment, the method of transmitting signals by wires by using the detector cable 526 is described. However, an exemplary embodiment is not limited thereto. Some or all of the signals may be transmitted wirelessly without using the detector cable 526.

The rotation plate 540 is disposed between the central member 521 and the first plate 530, and is fastened to a surface of the first plate 530 by using a plurality of fastening devices 542, for example, a clamping unit. A first slide rail 541 is formed on the rotation plate 540 along a cylindrical direction, and the first guide 522 may be disposed on the first slide rail 541 to control a rotation path of the first plate 530 and the rotation plate 540.

A rotation sensor or rotation sensors 550 may be disposed on the base 520 to sense whether the rotation plate 540 rotates and a rotation direction. According to an exemplary embodiment, the rotation sensor 550 may include an optical encoder or a magnetic encoder. For example, the rotation sensor 550 may include a first rotation sensor 551 and a second rotation sensor 552 which may be disposed apart from each other by a predetermined distance, along a cylindrical direction of the rotation plate 540. For example, when a plurality of input signals are received as the rotation plate 540 rotates, a user may analyze the input signals, which are sensed whether the rotation plate 540 rotates, and if the rotation plate 540 rotates, the user may know a rotation direction.

A detachment sensor 560 is configured to sense whether the X-ray detecting device 400 is mounted in the stand-type bucky 500. For example, if the detachment sensor 560 senses that the X-ray detecting device 400 is not mounted in the stand-type bucky 500, the controller unit 150 of FIG. 1 may block a signal for applying a voltage to the high-voltage generator 121 so that the X-ray emitter 120 does not emit X-rays. The detachment sensor 560 may include at least one of an optical and a magnetic sensor, but it is not limited thereto.

For example, as illustrated in FIG. 5D, the detachment sensor 560 may include an elastic member 562 which may be disposed on the central member 521 and may extend along a penetration hole formed in the first plate 530 and the rotation plate 540, a contact housing 561 of a cylindrical shape which is fastened to an end of the elastic member 562, and a plurality of guides 563 which may be disposed on an outer wall of the contact housing 561 and may guide a movement of the contact housing 561. Accordingly, when the X-ray detecting device 400 is disposed on the first plate 530, the detachment sensor 560 may sense whether the X-ray detecting device 400 is disposed on the first plate 530 by sensing a change in the elastic member 562.

The X-ray detecting device 400 may be charged by using wires by using the first terminal 421, and may also be charged wirelessly. Referring to FIGS. 4B and 5E, when the battery 430 is disposed to be eccentric from the center of the X-ray detecting device 400, a charger 440 may be disposed below the first plate 530 to correspond to a location of the battery 430. A first coil 441 formed as a square shape coil 443 and/or a circular shape coil 444 and an electric coil disposed on a charging pad 442 may be included in the charger 440, and the first coil 441 and the electric coil may interact with each other to generate an inducement current. The inducement current generated by the interaction of the first coil 441 and the electric coil may be received by the battery 430 so that the X-ray detecting device 400 may be charged wirelessly.

As the wireless charging of the X-ray detecting device 400 is possible, additional charging lines and terminals may be removed, to make a manufacturing process simple and reduce an overall size of a device. Also, while the X-ray imaging apparatus 200 performs imaging, charging may be continuously performed. Thus, the X-ray detecting device 400 does not additionally need to be separated for charging, and additional processes for charging may be omitted. Consequently, a user's convenience may be improved.

Locations of the charger 440 are not limited to the location below the first plate 530, and may vary in correspondence to a location of the battery 430. For example, referring to FIGS. 4C and 5F, the battery 430 may be disposed in a central portion of the X-ray detecting device 400, and in this case, the charger 440 may be disposed below the first plate 530 or below the rotation plate 540, to correspond to the location of the battery 430.

Figure 6A:
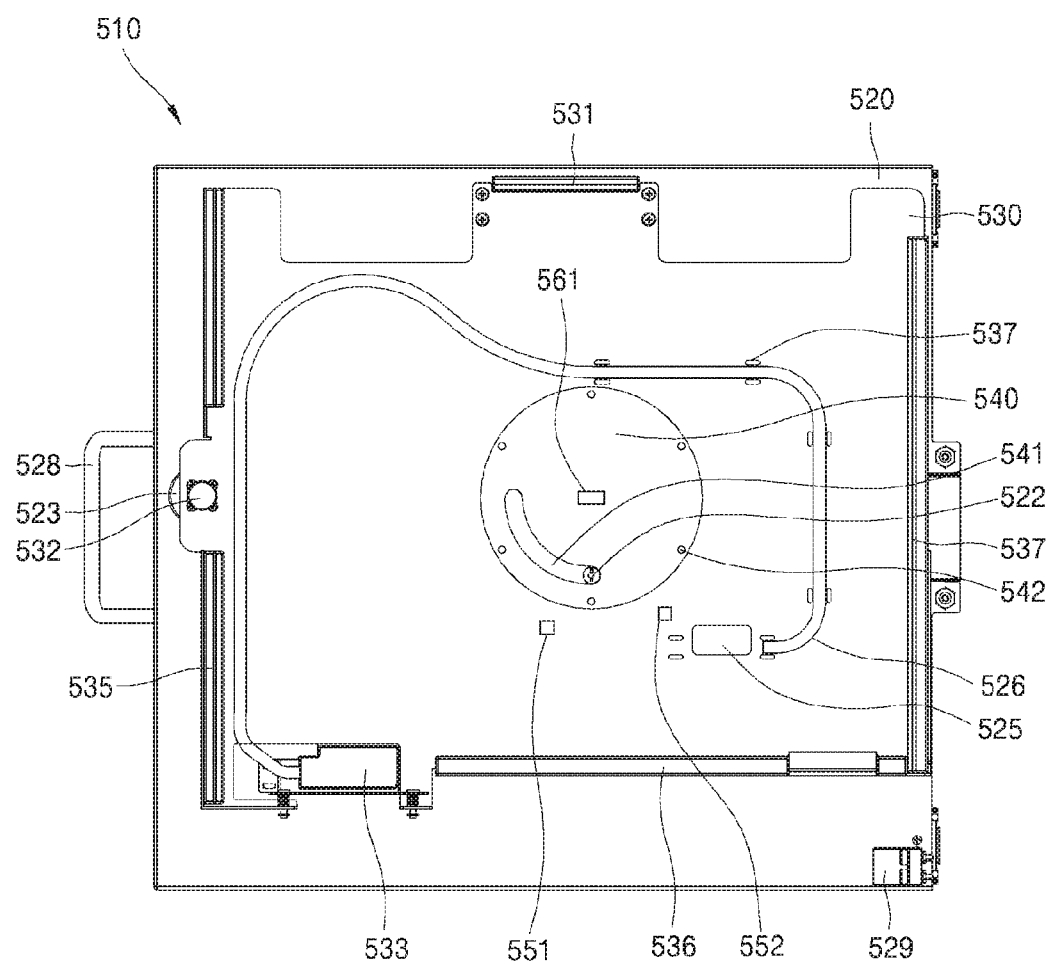
FIG. 6A is a plan view of a bucky tray according to an exemplary embodiment.
Figure 6B:
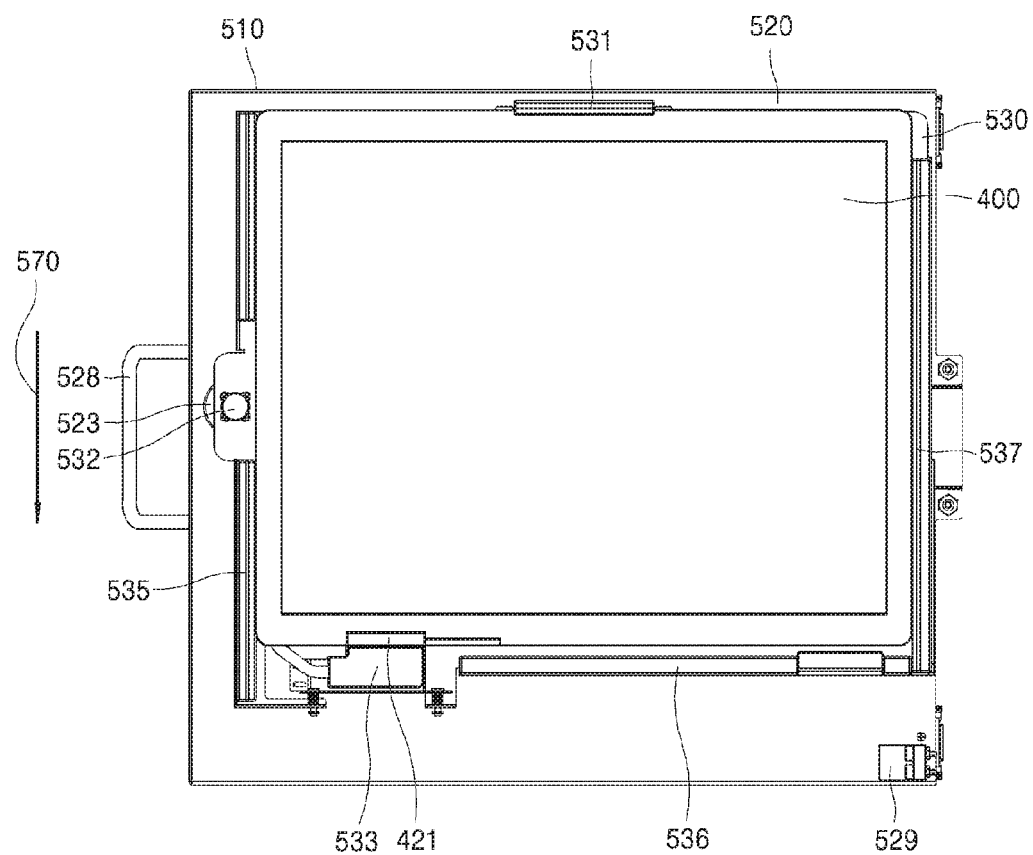
FIG. 6B is a plan view of a bucky tray in which an X-ray detecting device is arranged.

FIG. 6A is a plan view of the bucky tray 510 according to an exemplary embodiment, and FIG. 6B is a plan view of the bucky tray 510 on which the X-ray detecting device 400 is disposed.

Referring to FIGS. 6A and 6B, an X-ray detecting device 400 having a size of 17×14 inches may be disposed on the bucky tray 510 in a first direction 570. When the X-ray detecting device 400 is disposed in the first direction, the first stopper 523 of the base 520 and the second stopper 532 of the first plate 530 are coupled to each other. Thus, a rotation of the first plate 530 with respect to the base 520 is restricted so that a relative location of the first plate 530 with respect to the base 520 is fixed. In the present exemplary embodiment, the X-ray detecting device 400 has the size of 17×14 inches. However, an exemplary embodiment is not limited thereto, and the X-ray detecting device 400 of other sizes may be disposed on the bucky tray 510.

When the X-ray detecting device 400 is disposed on the bucky tray 510, a bottom surface portion of the X-ray detecting device 400 may contact an end of the contact housing 561 of the detachment sensor 560, to apply a pressure to the contact housing 561, as illustrated in FIG. 5D. The elastic member 562 which is disposed such that an end thereof is fastened to the contact housing 561 may also receive a compressive force, and the shape thereof may be changed. By measuring such a change in the shape of the elastic member 562, the detachment sensor 560 may sense whether the X-ray detecting device 400 is disposed on the first plate 530.

When an X-ray examination is performed by using the stand-type bucky 500, a center of the stand-type bucky 500 and a center of the X-ray detecting device 400 mounted on the bucky tray 510 have to correspond to each other in a fixed state. A user sets a location of a patient based on the center of the stand-type bucky 500 to perform the examination, and thus, if the center of the X-ray detecting device 400 and the center of the stand-type bucky 500 do not correspond to each other, a center of an obtained image is biased to one side to make the image less worthy for a diagnosis.

In order to make the centers of the stand-type bucky 500 and the X-ray detecting device 400 correspond to each other, the plurality of location guides 535, 536, and 537 of bar shapes are disposed at a side portion of the rotation plate 540. When the X-ray detecting device 400 is disposed on the bucky tray 510, the user may adjust relative locations of the bucky tray 510 and the X-ray detecting device 400 by using the plurality of location guides 535, 536, and 537 so that the centers of the stand-type bucky 500 and the X-ray detecting device 400 are made to correspond to each other. Then, a side portion of the sensor case 420 is fastened on the first plate 530 by using the first fastener 531 so that the X-ray detecting device 400 is fastened on the bucky tray 510.

Figure 7A:
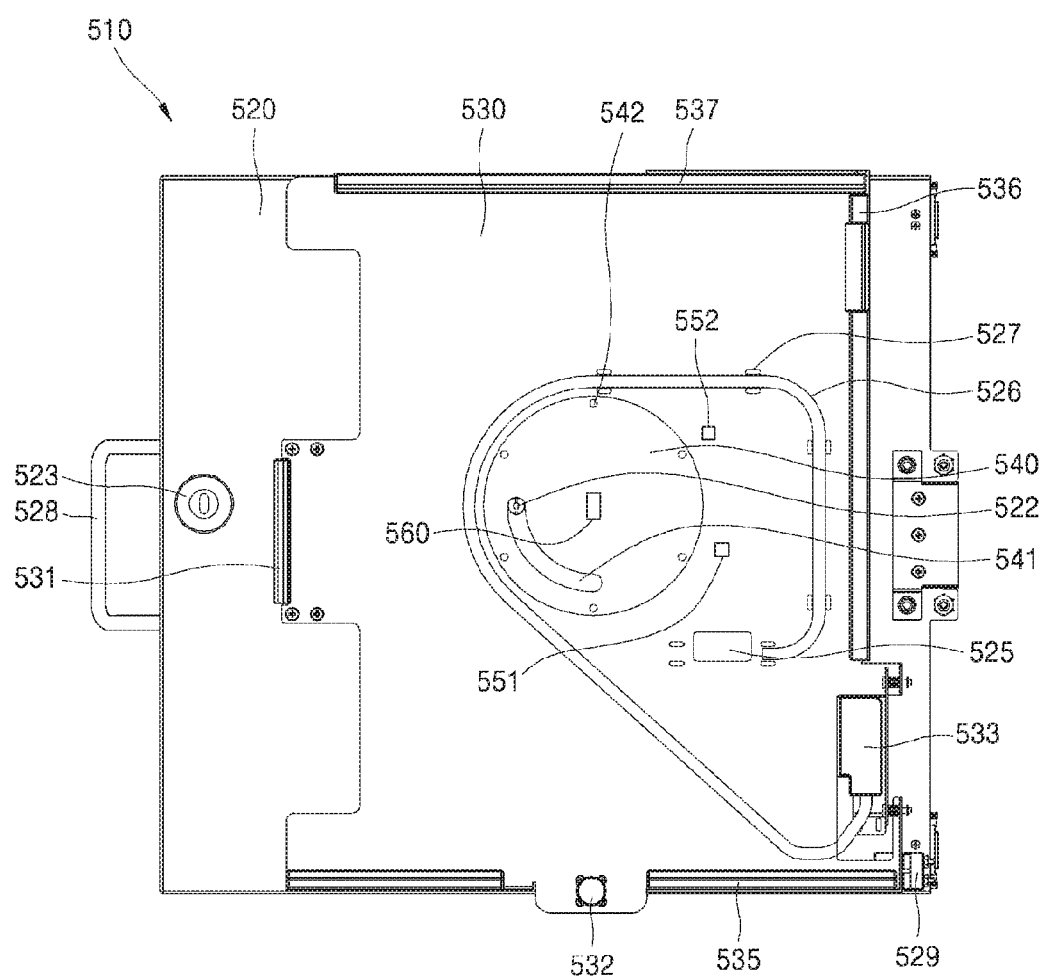
FIG. 7A is a plan view of a bucky tray according to an exemplary embodiment.
Figure 7B:
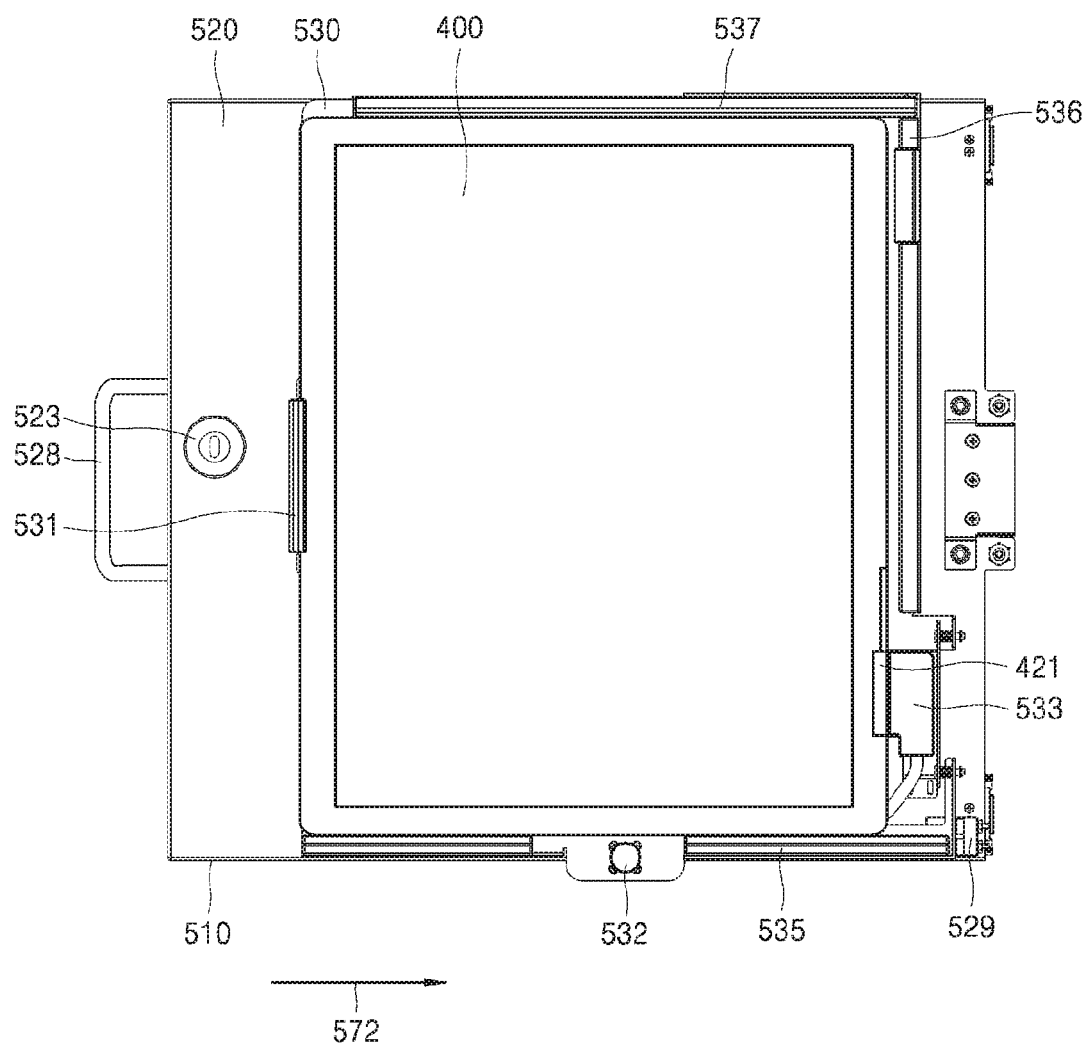
FIG. 7B is a plan view of a bucky tray in which an X-ray detecting device is arranged.
Figure 8:
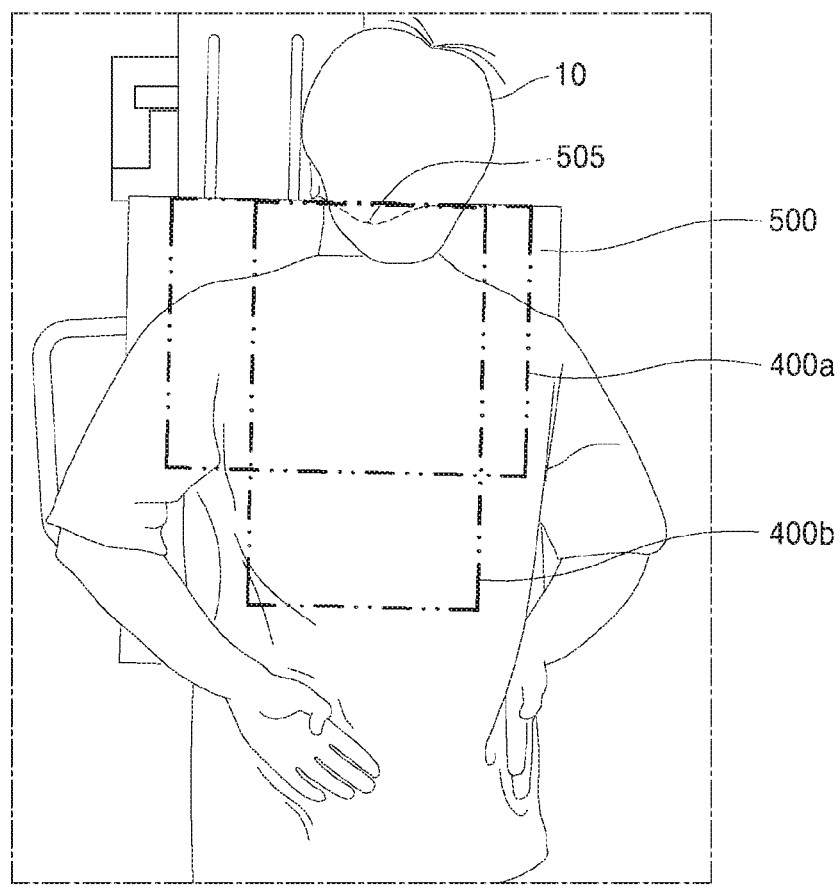
FIG. 8 is a view of an example in which an object is diagnosed by using a stand-type bucky according to an exemplary embodiment.

FIG. 7A is a plan view of the bucky tray 510 according to an exemplary embodiment, and FIG. 7B is a plan view of the bucky tray 510 on which the X-ray detecting device 400 is disposed. FIG. 8 illustrates an example in which the object 10 is diagnosed by using the stand-type bucky 500.

According to a diagnostic purpose of the X-ray detecting device 400, a location of the X-ray detecting device 400 may also be changed. For example, for the X-ray imaging apparatus 200 using the stand-type bucky 500 as illustrated in FIG. 8, a diagnostic area may vary according to the diagnostic purpose. The X-ray detecting device 400 may be disposed to be rotatable in order to specify the diagnostic area.

Referring to FIGS. 7A and 7B, the X-ray detecting device 400 of 17×14 inches is disposed on the bucky tray 510 in a second direction 572 which is a direction that is rotated by 90 degrees from the first direction in a counter clockwise direction. However, this is not limiting and a rotation angle may be different from 90 degrees and/or a rotation direction may be different from a counter clockwise direction. In order to rotate the X-ray detecting device 400 in the second direction, the coupling of the first stopper 523 and the second stopper 532 may be released. The rotation plate 540 and the first plate 530 may rotate in a counter clockwise direction due to an external force by a user or a weight of the first plate 530, for example, from a first state of FIG. 6A to a second state of FIG. 7A, i.e., from a first position to a second position. A rotation path of the first plate 530 may be controlled as the rotation plate 540 moves along the first slide rail 541 by the first guide 522 provided on the base 520. When the first plate 530 reaches the second state, the stopping protrusion 529 provided on the base 520, for example, as the permanent magnet and a side portion of the first plate 530 are coupled to each other, and thus, relative locations of the base 520 and the first plate 530 are fastened in the second state. The process of fastening the X-ray detecting device 400 on a central position of the bucky tray 510 by using the plurality of location guides 535, 536, and 537, and the first fastener 531 is the same as the process in the exemplary embodiment illustrated in FIGS. 6A and 6B, and thus, its description will be omitted.

As the first plate 530 rotates to the second state from the first state, the second terminal 533 fastened to the first plate 530 also rotates in a counter clockwise direction. Thus, even if the arrangement of the X-ray detecting device 400 is changed, the first terminal 421 and the second terminal 533 can be easily connected to each other. In addition, since the detector cable 526 may also slide along a guide line formed along the plurality of cable fasteners 527 and a side portion of the rotation plate 540, the detector cable 526 may extend such that an end thereof is connected to the second terminal 533, without twists.

With reference to FIGS. 5D and 8, the center Y of the central member 521 is eccentric from the center X of the base 520. When the first plate 530 against which the X-ray detecting device 400 is supported rotates from the first state to the second state, a side portion of an X-ray detecting device in the first state (reference numeral 400a) and an X-ray detecting device in the second state (reference numeral 400b) may be aligned with the edge of the object support 505 formed on the stand-type bucky 500. That is, as illustrated in FIG. 8, when the object 10 maintains a straight standing position while a chin thereof is supported by the object support 505, a side portion of the first plate 530 on which the first fastener 531 illustrated in FIG. 6A is disposed and a side portion of the first plate 530 on which the location guide 537 illustrated in FIG. 7A is disposed may be aligned with the edge of the object support 505. Thus, even if the first plate 530 rotates from the first state to the second state, imaging of a chest of the object 10 may be performed accurately.

The plurality of rotation sensors 551 and 552 may sense the rotation of the rotation plate 540 in order to sense that the first plate 530 rotates from the first state to the second state. For example, as illustrated in FIGS. 6A and 7A, the first rotation sensor 551 and the second rotation sensor 552 may be disposed apart from each other by a predetermined distance along a cylindrical direction of the rotation plate 540. When the rotation plate 540 rotates so that the first plate 530 rotates from the first state to the second state, the first rotation sensor 551 and the second rotation sensor 552 formed as magnetic encoders or optical encoders may sense periodic signals with respect to the rotation of the rotation plate 540, from a predetermined device arranged in a circumferential portion of the rotation plate 540, for example, a permanent magnet or a mirror portion, and the first rotation sensor 551 and the second rotation sensor 552 may analyze whether there are input signals, and an order of the input signals, in order to determine whether the first plate 530 rotates, and a rotation direction of the first plate 530.

When the arrangement of the X-ray detecting device 400 is changed as the first plate 530 rotates from the first state to the second state, or when it is not recognized that the X-ray detecting device 400 is not arranged in the stand-type bucky 500, unnecessary exposure may occur to a patient. With regard to this, the rotation sensor 550 for sensing whether the first plate 530 rotates, and the detachment sensor 560 for sensing whether the X-ray detecting device 400 is mounted are arranged to sense whether the X-ray detecting device 400 is mounted and an arrangement location, and sensing signals sensed by the rotation sensor 550 and the detachment sensor 560 may be transmitted to the controller 150. The controller 150 may receive the sensing signals from the rotation sensor 550 and the detachment sensor 560 and may generate a control signal according to a mounting state of the X-ray detecting device 400.

For example, the control signal generated by the controller 150 may be transmitted to the X-ray emitter 120, and the X-ray emitter 120 may determine whether to emit X-rays to the area in which the X-ray detecting device 400 is mounted, according to the received control signals. Also, when the X-ray detecting device 400 is changed from the first state to the second state, the controller 150 may move the X-ray emitter 120 by using the motors 211, 212, and 213 illustrated in FIG. 2, to adjust an exposure range. Accordingly, unnecessary exposure which may be applied to the object 10 may be reduced.

Figure 9A:
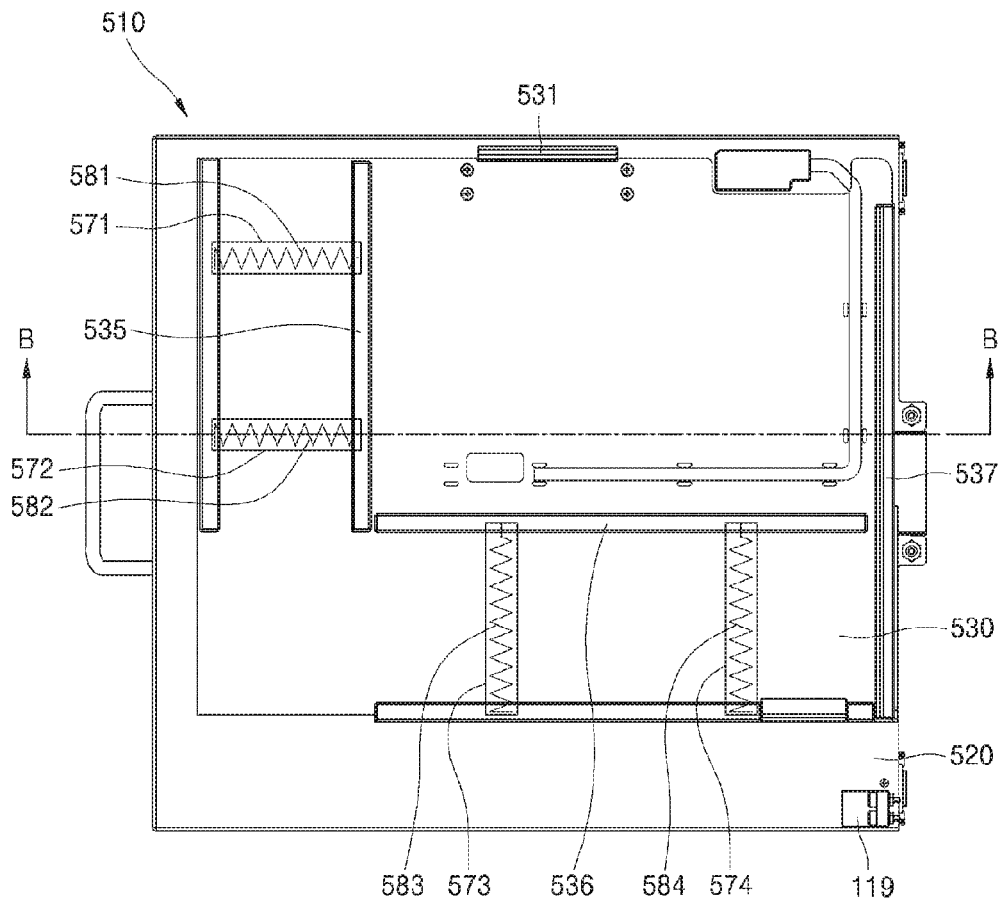
FIG. 9A is a plan view of a bucky tray according to an exemplary embodiment.
Figure 9B:
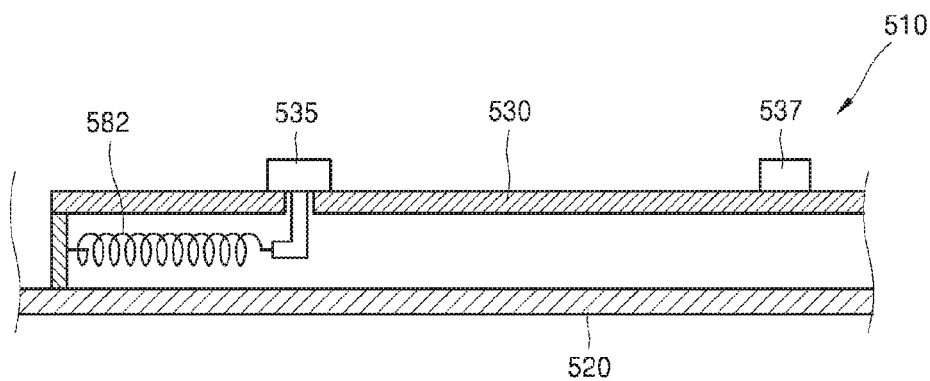
FIG. 9B is a cross-sectional view taken along line B-B of the bucky tray of FIG. 9A.
Figure 9C:
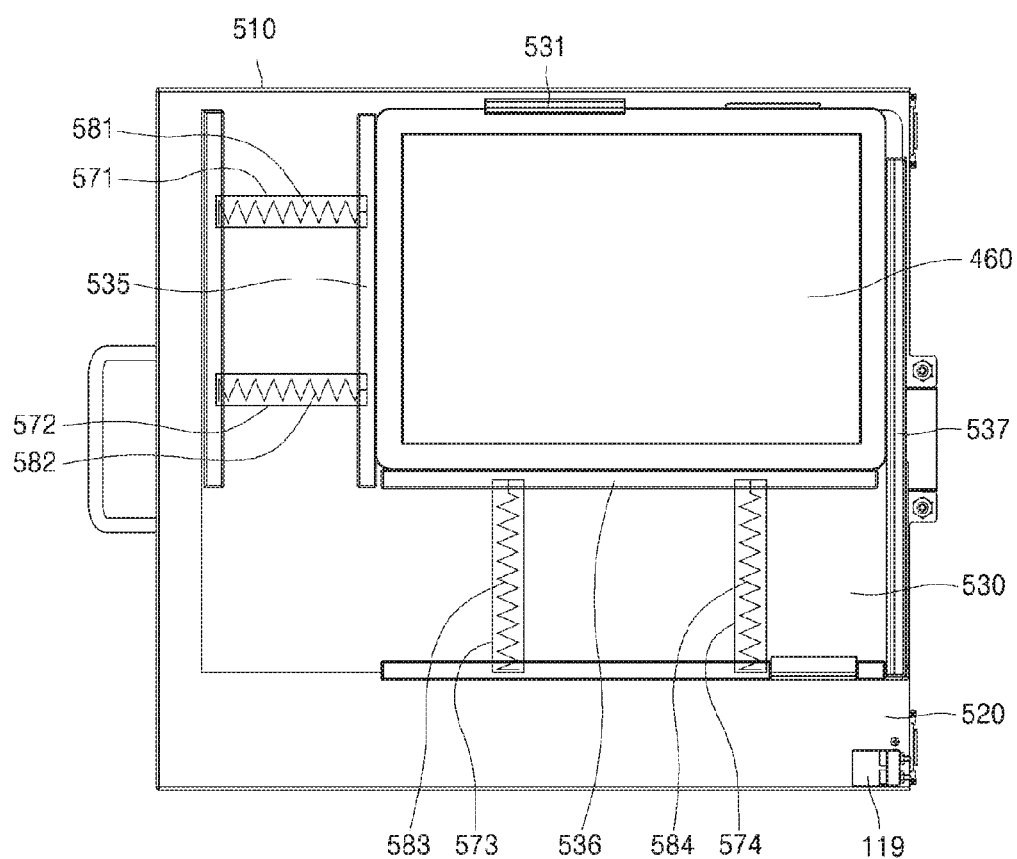
FIG. 9C is a plan view of a bucky tray in which an X-ray detecting device is arranged.

FIG. 9A is a plan view of the bucky tray 510 according to an exemplary embodiment, FIG. 9B is as cross-sectional view taken along line B-B of the bucky tray 510 of FIG. 9A, and FIG. 9C is a plan view of the bucky tray 510 on which the X-ray detecting device 400 is disposed.

The X-ray imaging apparatus 200 may use different field of view (FOV) according to diagnostic purposes, and may irradiate X-rays to a relatively large area or a relatively small area, according to the FOV. To provide the FOV of a specific size, various sizes of the X-ray detecting device 400 may be inserted into the stand-type bucky 500.

Referring to FIGS. 9A and 9B, an X-ray detecting device 400 of a size of 8×10 inches, for example, a small area X-ray detecting device 460 may be disposed on the bucky tray 510. In order to fasten the small area X-ray detecting device 460 having a relatively small incident area on the first plate 530, the first location guide 535 and the second location guide 536 may be disposed on the first plate 530 to be able to slide.

A plurality of elastic members 581 through 584 may be disposed between the first plate 530 and the base 520 as illustrated in FIG. 9B. The first elastic member 581 and the second elastic member 582 may be disposed apart from each other with a predetermined distance therebeween, and the third elastic member 583 and the fourth elastic member 584 may be disposed apart from each other with a predetermined distance therebetween. An end of the first elastic member 581 and an end of the second elastic member 582 may be fastened to the first location guide 535, and the other end of the first elastic member 581 and the other end of the second elastic member 582 may be fastened to a support fastened to the first plate 530. An end of the third elastic member 583 and an end of the fourth elastic member 584 may be fastened to the second location guide 536 and the other end of the third elastic member 583 and the other end of the fourth elastic member 584 may be fastened to the support fastened to the first plate 530.

When the small area X-ray detecting device 460 is disposed on the first plate 530, the first through fourth elastic members 581 through 584 are not compressed. Accordingly, the first location guide 535 and the second location guide 536 may maintain the state illustrated in FIG. 9A to support the X-ray detecting device 460 on the first plate 530.

On the contrary, when the X-ray detecting device 400 having a relatively large incident area, for example, the X-ray detecting device 400 of 14×17 inches is disposed on the first plate 530, the first through fourth elastic members 581 through 584 may be compressed. Accordingly, the first location guide 535 and the second location guide 536 may maintain the state illustrated in FIG. 6A to support the X-ray detecting device 400 having a relatively large incident area on the first plate 530.

Figure 10A:
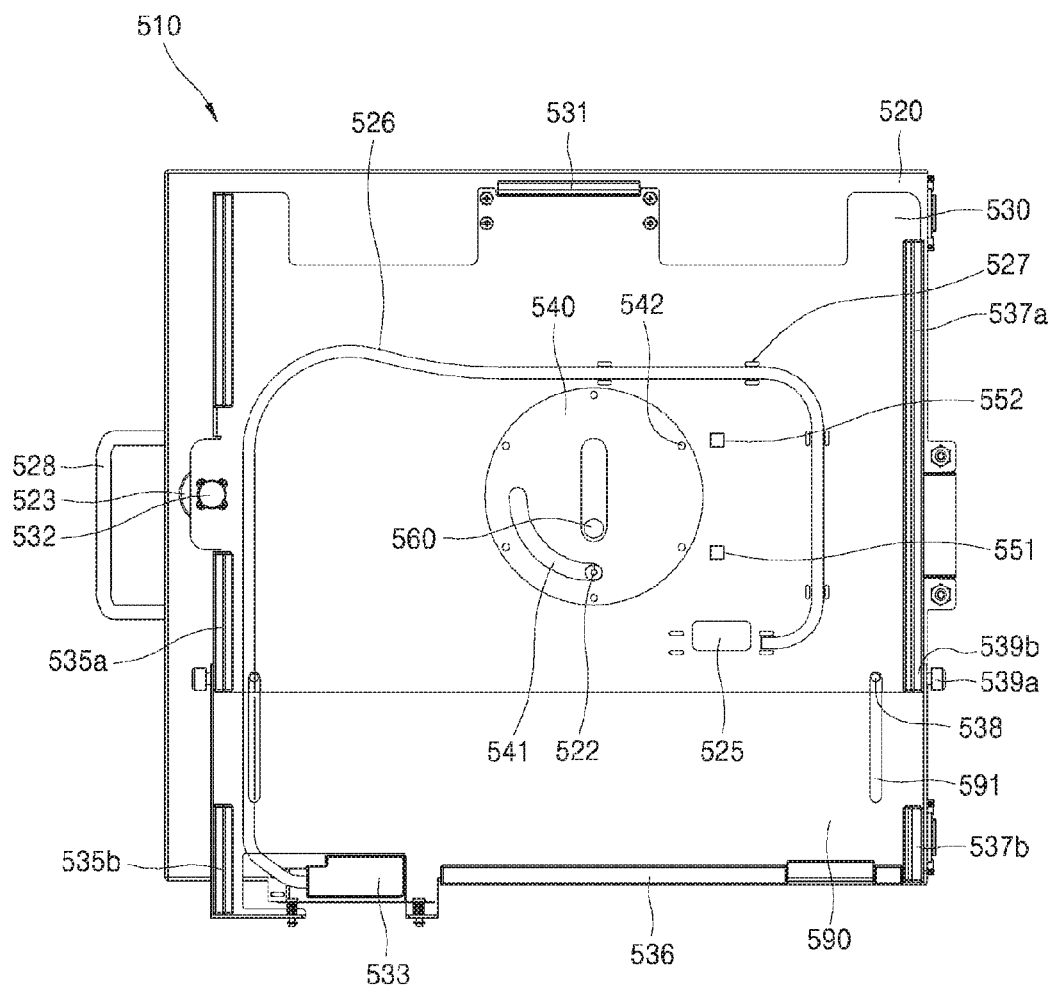
FIG. 10A is a plan view of a bucky tray according to an exemplary embodiment.
Figure 10B:
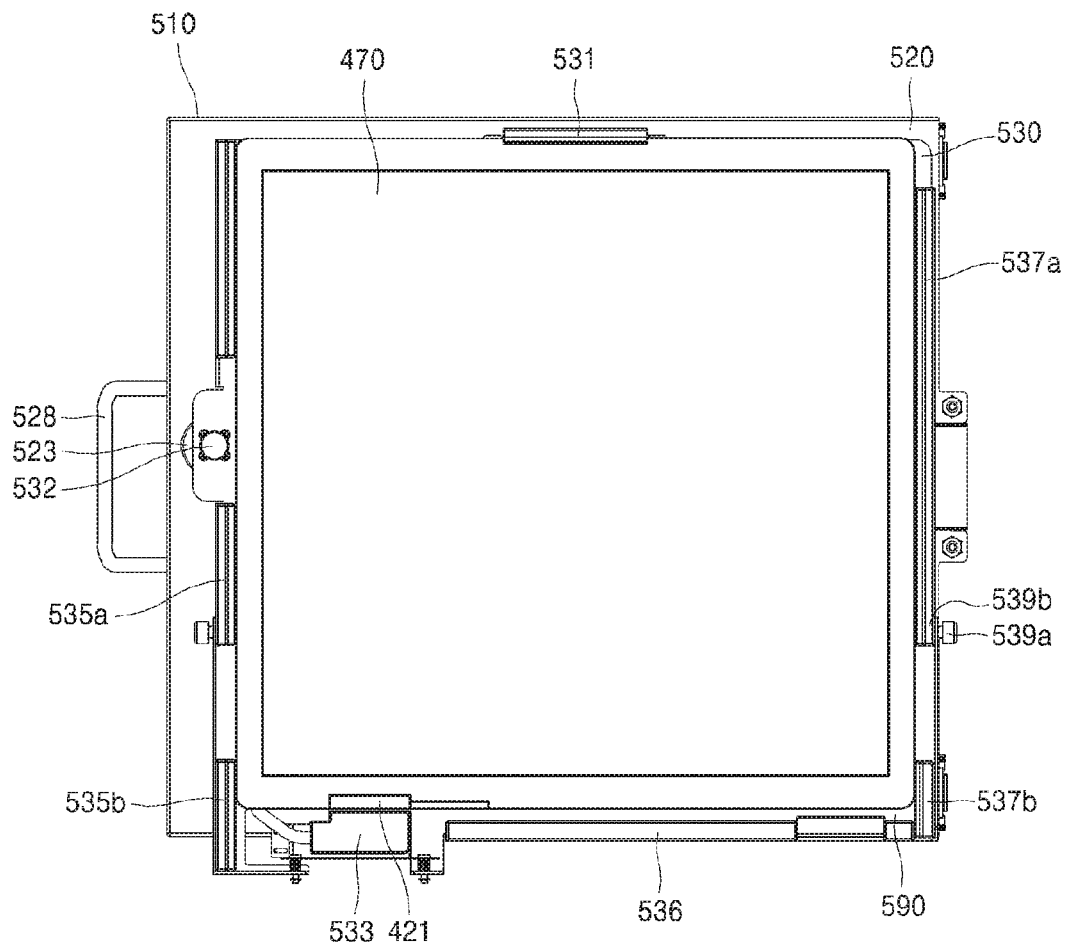
FIG. 10B is a plan view of a bucky tray in which an X-ray detecting device is arranged.

FIG. 10A is a plan view of the bucky tray 510 according to an exemplary embodiment, and FIG. 10B is a plan view of the bucky tray 510 on which the X-ray detecting device 400 is disposed.

In order to emit X-rays to a relatively large area according to the diagnostic purpose, a larger X-ray detecting device 400, for example, a large area X-ray detecting device 470 having a large X-ray incident area may be used. Referring to FIGS. 10A and 10B, the large area X-ray detecting device 470, for example, the large area X-ray detecting device 470 of 17×17 inches may be disposed on the bucky tray 510. In order to dispose the large area X-ray detecting device 470 which is larger than the X-ray detecting device 400 of 14×17 inches illustrated in FIG. 6A, a second plate 590, which is a plate member, may be disposed between the base 520 and the first plate 530. A second guide rail 591 is disposed on the second plate 590 and a second guide 538 is disposed on a rear surface of the first plate 530. The second plate 590 may be accommodated in and discharged from a first location in which the X-ray detecting device of a first size may be accommodated and a second location in which the X-ray detecting device of a second size may be accommodated, between the base 520 and the first plate 530 by the second guide 538 and the second guide rail 591.

A first slide fastener 539a is formed as a hinge structure which is movable in an axis direction to both ends of the first plate 530. The first slide fastener 539a is inserted into a second slide fastener 539b provided in the first plate 530 as a through-hole shape, and thus, the accommodation or the discharge of the first slide fastener 539a to or from a first location or a second location of the second plate 590 is completed. Accordingly, a relative location of the second plate 590 with respect to the first plate 530 is fastened. Also, location guides 535a and 537b may be additionally formed along the second plate 590 to adjust a location of the X-ray detecting device. Then, a process of fastening the X-ray detecting device on a central position of the bucky tray 510 by using the plurality of location guides 535a, 535b, 536, 537a, and 537b, and the first fastener 531 is the same as the process in the exemplary embodiment described with reference to FIGS. 5A-8, and thus, its description will be omitted.

The second terminal 533 may be disposed at a side portion of the second plate 590. Thus, even when the second plate 590 is discharged, the first terminal 421 and the second terminal 533 may be easily connected to each other.

As described above, regardless of the location at which the X-ray detecting device 400 is fastened, and the size of the X-ray detecting device 400, the X-ray detecting device 400 may be accommodated and an X-ray examination may be performed by using the single bucky tray 510, and thus, a user may freely use the X-ray detecting device 400 of a required type. A connection terminal may be disposed at a side portion of the first plate 530 or the second plate 590 to prevent twists of the detector cable 526 connected to the outside, and thus, regardless of the arrangement of or the type of the X-ray detecting device 400, the X-ray detecting device 400 may be easily connected to an external device.

Figure 11:
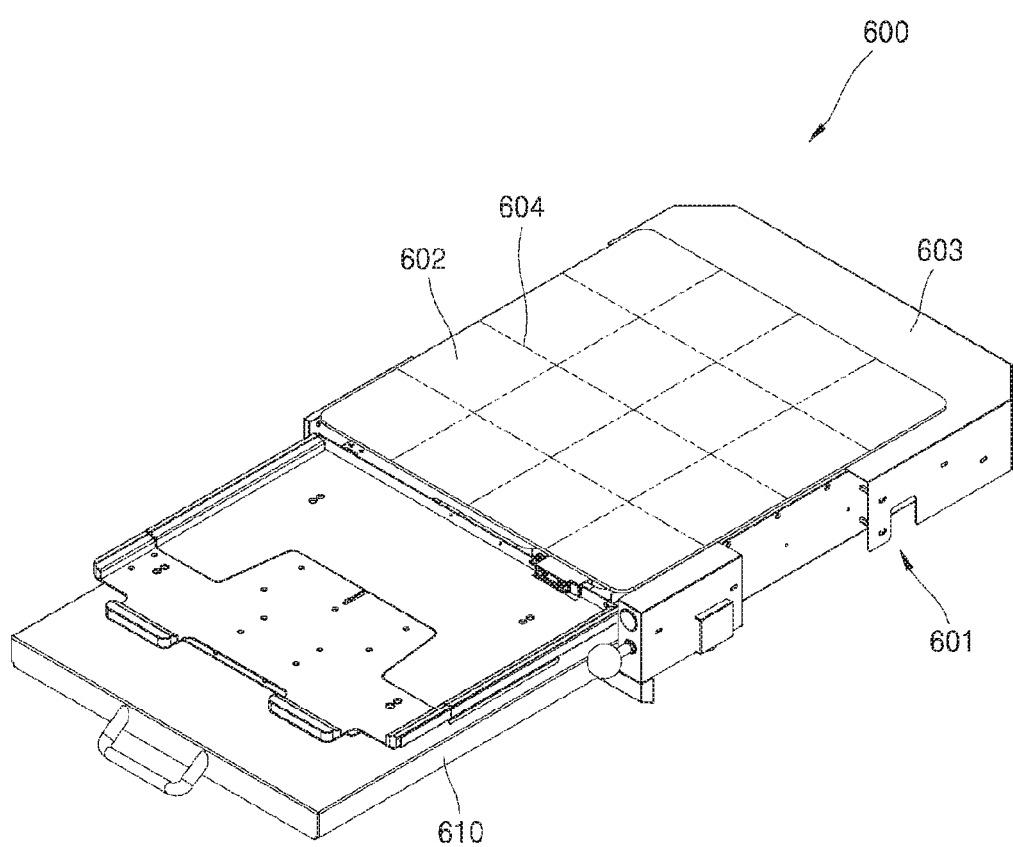
FIG. 11 is a perspective view of a table-type bucky according to an exemplary embodiment.
Figure 12:
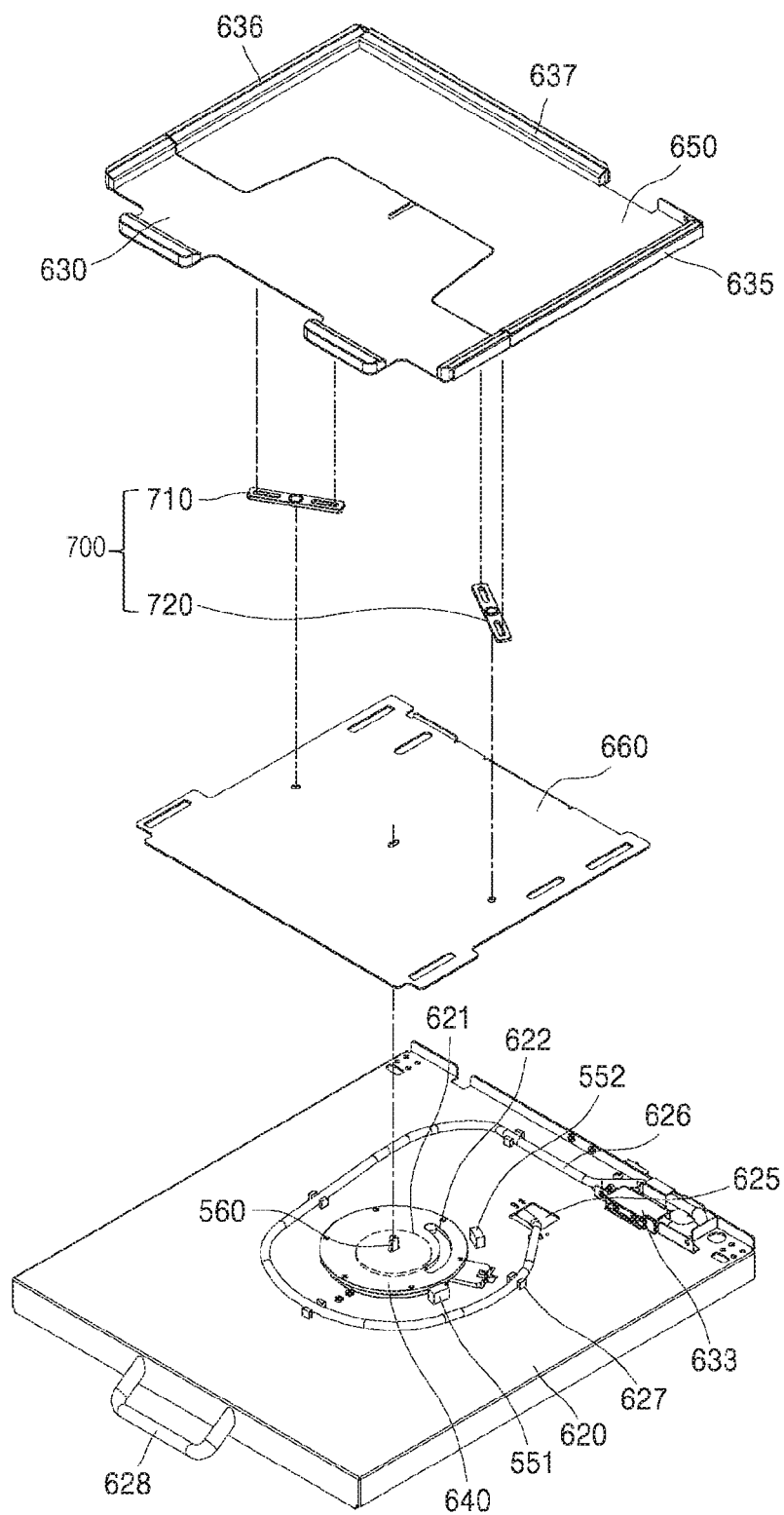
FIG. 12 is an exploded perspective view of the table-type bucky of FIG. 11.

FIG. 11 is a perspective view of a table-type bucky 600 according to an exemplary embodiment, and FIG. 12 is an exploded perspective view of the table-type bucky 600 of FIG. 11. For convenience of explanation, components of the table-type bucky 600, which are the same as the components of the stand-type bucky 500, will not be repeatedly described.

The X-ray imaging apparatus 200 may include the X-ray detecting device 400 and the table-type bucky 600 configured to support the X-ray detecting device 400. Referring to FIGS. 11 and 12, the table-type bucky 600 may include a bucky tray 610 for attaching and detaching the X-ray detecting device 400, and an accommodation unit 601 for accommodating the X-ray detecting device 400. The accommodation unit 601 is an accommodation member for accommodating the X-ray detecting device 400 and may include an incident surface 602, a chamber 603, and a grid 604 which is disposed in parallel to the incident surface 602 at a backward portion of the incident surface 602. Unlike the stand-type bucky 500, the table-type bucky 600 may be disposed on a table by which the object 10 is supported, and thus, the accommodation unit 601 of the table-type bucky 600 does not include an additional object support.

The bucky tray 610 may be accommodated in and discharged from the accommodation unit 601, and may include a base 620, and a first plate 630 and a second plate 650 which are disposed on the base 620 to be rotatable. The base 620 is a plate member, and on a surface of the base 620, a central member 621 of a cylindrical shape extending in an X-ray emission direction, a first guide 622, a penetration hole 625 through which a detector cable 626 of the X-ray detecting device 400 can penetrate, a second terminal 633 which may be connected to the first terminal 421 of the X-ray detecting device 400, the detector cable 626 which is connected to the second terminal 633 to transmit electrical signals detected from the X-ray detecting device 400 to the outside, and a plurality of cable fasteners 627 for preventing twists of the detector cable 626 are provided. A handle 628 of a link shape may be disposed at a side portion of the base 620, and the bucky tray 610 may be easily accommodated in and discharged from the accommodation unit 601 by using the handle 628.

Unlike the stand-type X-ray imaging apparatus 200 illustrated in FIG. 8, for the table-type X-ray imaging apparatus 200, imaging may be performed at a central portion of the table-type bucky 600, and the central member 621 of the table-type bucky 600 may be formed at a central portion of the base 620. Accordingly, even if the X-ray detecting device 400 is disposed in the table-type bucky 600 at a different angle, the X-ray detecting device 400 may be disposed at the central portion of the base 620.

The first plate 630 and the second plate 650 are plate members on which the X-ray detecting device 400 is mounted. The first plate 630 and the second plate 650 may be disposed to be rotatable with respect to the base 620. A portion of the first plate 630 may be disposed below the second plate 650 and may slide with respect to the second plate 650. On a surface of the first plate 630 and the second plate 650 on which the X-ray detecting device 400 is disposed, a plurality of location guides 635, 636, and 637 for adjusting a location of the X-ray detecting device 400 may be disposed along a side portion of the first plate 630 and the second plate 650.

As described above, unlike the stand-type X-ray imaging apparatus 100, for the table-type X-ray imaging apparatus 100, imaging may be performed at a central portion of the table-type bucky 600. Thus, if the large area X-ray detecting device 400 which has a relatively large incident area is disposed in the stand-type bucky 600, the first plate 630 and the second plate 650 have to move symmetrically so that the arrangement of the X-ray detecting device 400 and the object 10 are not misaligned.

A movement guide 700 may connect the movement of the first plate 630 and the second plate 650 to make the first plate 630 and the second plate 650 move symmetrically. For example, referring to FIG. 12, a middle plate 660 fastened to the first plate 630 and the second plate 650 may be disposed between the first and second plates 630 and 650 and the base 620, and a first movement guide 710 and a second movement guide 720 may be symmetrically disposed between the first and second plates 630 and 650 and the middle plate 660.

Figure 13A:
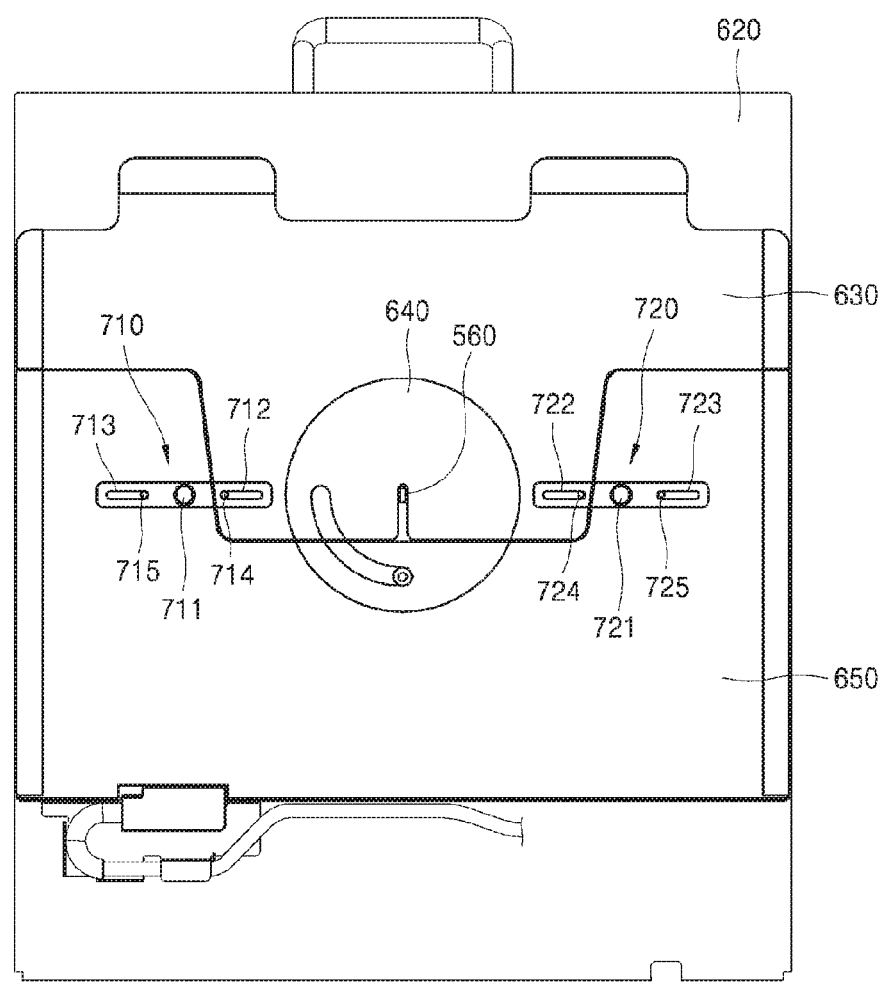
FIGS. 13A and 13B are plan views of a table-type bucky according to an exemplary embodiment.
Figure 13B:
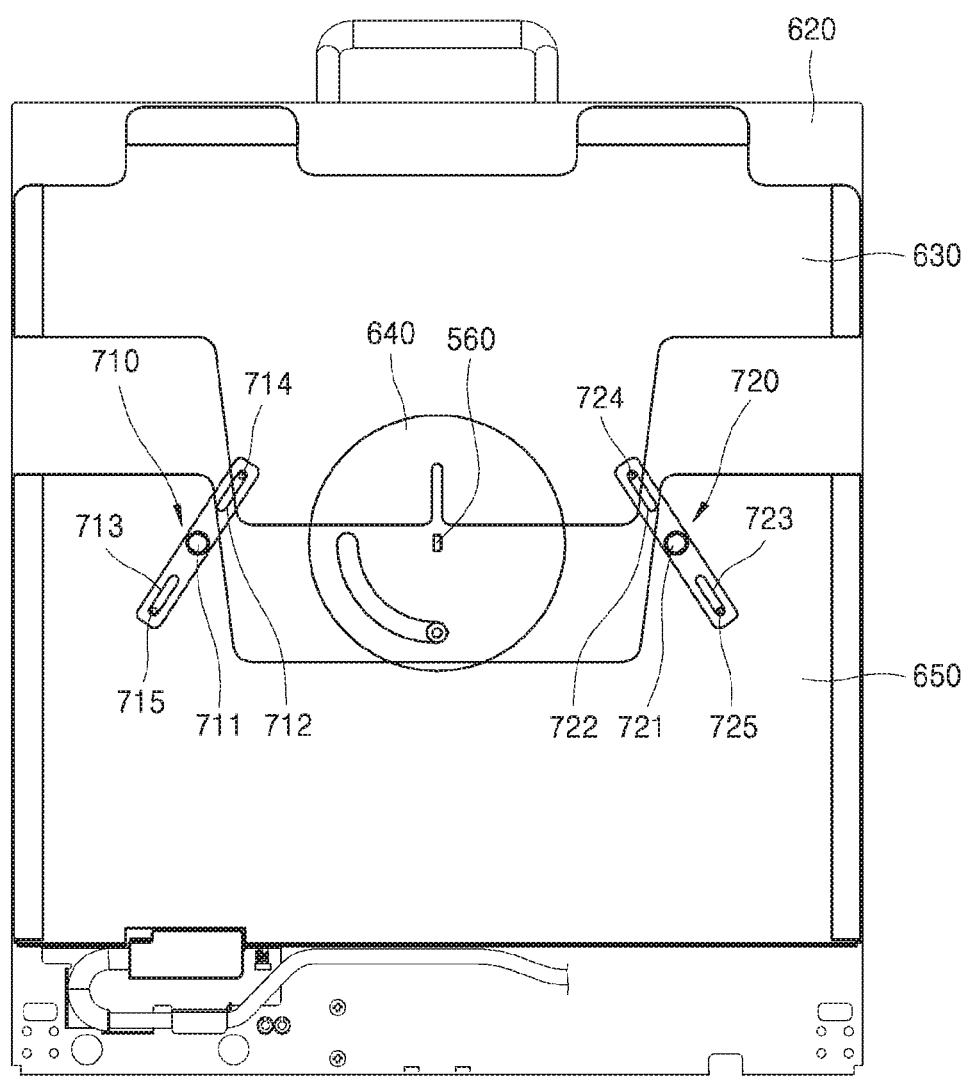

FIGS. 13A and 13B are plan views of the table-type bucky 600 according to an exemplary embodiment.

The first movement guide 710 and the second movement guide 720 may include rotation axes 711 and 721 disposed to be fastened to the middle plate 660, a plurality of first slide rails 712 and 713 extending from the rotation axis 711 in directions in which the plurality of first slide rails 712 and 713 are opposite to each other, a plurality of second slide rails 722 and 723 extending from the rotation axis 721 in directions in which the plurality of second slide rails 722 and 723 are opposite to each other, a plurality of first guides 714 and 724 fastened to the first plate 630 to be able to slide with respect to the first slide rail 712 and the second slide rail 722, respectively, and a plurality of second guides 715 and 725 fastened to the second plate 650 to be able to slide with respect to the first slide rail 713 and the second slide rail 723, respectively.

A rotation plate 640 is disposed between the central member 621 and the middle plate 660, and is fastened to a surface of the middle plate 660 by using one or more fastening devices, for example, a clamping unit. A first slide rail 641 may be formed on the rotation plate 640 along a cylindrical direction and the first guide 622 may be disposed on the first slide rail 641 to control a rotation path of the first plate 630, the second plate 650, and the rotation plate 640.

When the large area X-ray detecting device 470 is disposed on the bucky tray 610, the first plate 630 and the second plate 650 may slide along opposite directions. For example, when a force is applied from the outside to withdraw the first plate 630 from the second plate 650, the first guides 714 and 724 fastened to the first plate 630 may also move along the first slide rail 712 and the second slide rail 722. Accordingly, the first slide rails 712 and 713 may rotate in a counter clockwise direction along the first rotation axis 711, and the second slide rails 722 and 723 may rotate in a clockwise direction along the second rotation axis 721.

As the first slide rails 712 and 713 and the second slide rails 722 and 723 rotate, the second guides 715 and 725 disposed in the first slide rail 713 and the second slide rail 723 may also move along the first slide rail 713 and the second slide rail 723. Accordingly, the second plate 650 fastened to the second guides 715 and 725 may also move symmetrically in a direction opposite to the direction in which the first plate 630 moves.

Figure 14A:
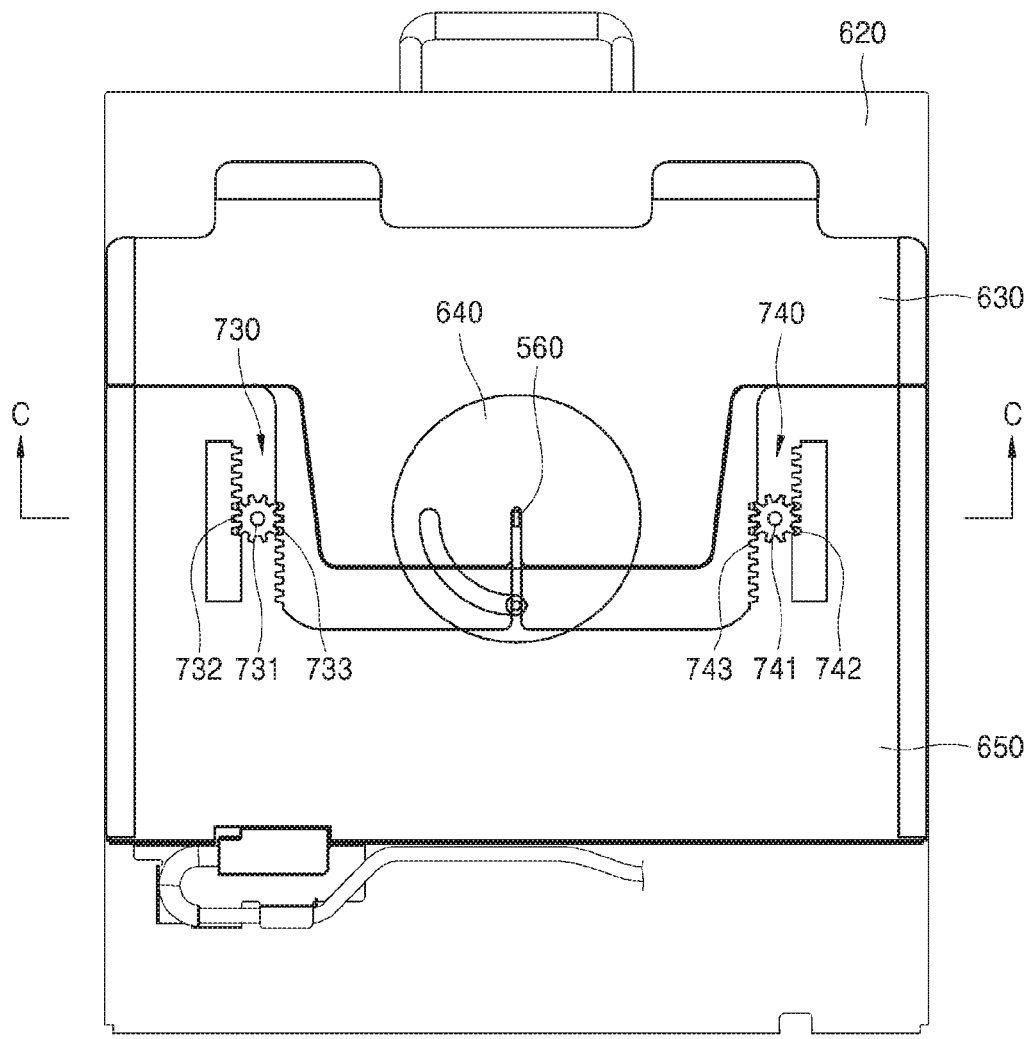
FIG. 14A is a plan view of a table-type bucky according to an exemplary embodiment.
Figure 14B:
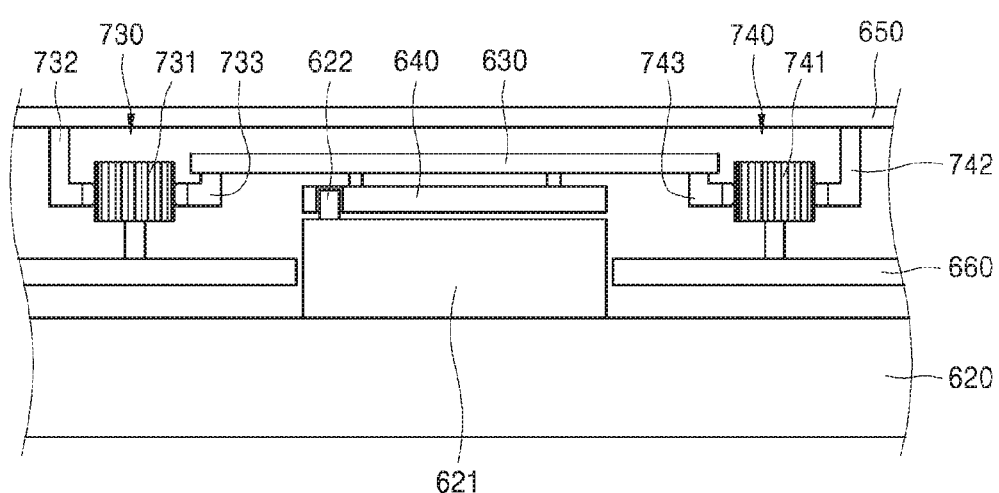
FIG. 14B is a cross-sectional view taken along line C-C of the table-type bucky of FIG. 14A.
Figure 14C:
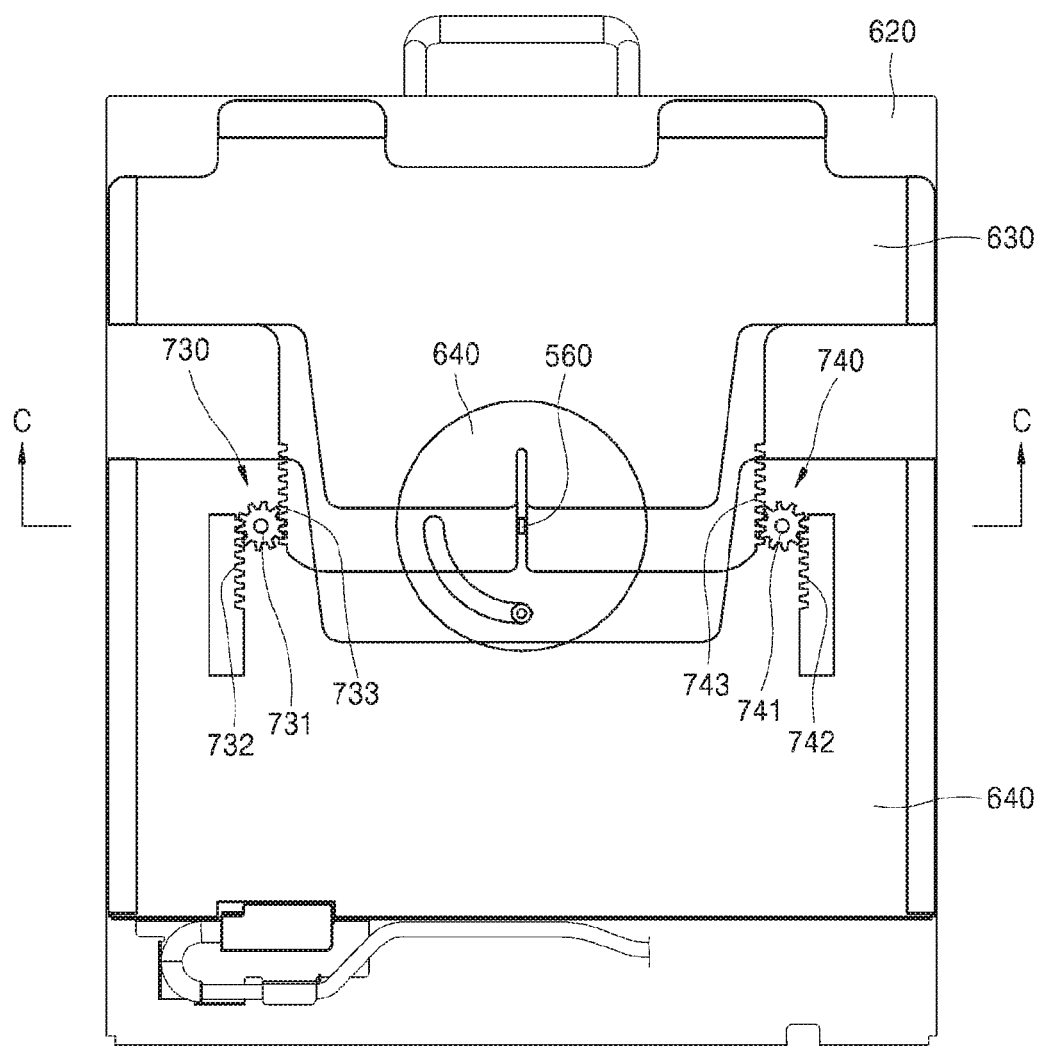
FIG. 14C is a plan view of a table-type bucky according to an exemplary embodiment.

FIG. 14A is a plan view of the table-type bucky 600 according to an exemplary embodiment. FIG. 14B is a cross-sectional view taken along line C-C of the table-type bucky 600 illustrated in FIG. 14A. FIG. 14C is a plan view of the table-type bucky 600 according to an exemplary embodiment.

The movement guide 700 which may connect the movement of the first plate 630 and the second plate 650 to make the first plate 630 and the second plate 650 move symmetrically may be formed by using a plurality of gear units. For example, referring to FIGS. 14A and 14B, the middle plate 660 fastened to the first plate 630 and the second plate 650 may be disposed between the first and second plates 630 and 650 and the base 620. A third movement guide 730 and a fourth movement guide 740 may be symmetrically disposed between the first and second plates 630 and 650 and the middle plate 660.

The third movement guide 730 and the fourth movement guide 740 may include a first pinion gear 731 and a second pinion gear 741 fastened to the middle plate 660, a first rack gear 732 and a second rack gear 733 disposed to interlock with the first pinion gear 731, and a third rack gear 742 and a fourth rack gear 743 disposed to interlock with the second pinion gear 732. The first rack gear 732 and the third rack gear 742 may be fastened to a lower surface of the second plate 650, and the second rack gear 733 and the fourth rack gear 743 may be fastened to a portion of the first plate 630.

Referring to FIGS. 14A and 14C, when the large area X-ray detecting device 470 is disposed on the bucky tray 610, the first plate 630 and the second plate 650 may slide in opposite directions. For example, when a force to withdraw the first plate 630 from the second plate 650 is applied from the outside, the second rack gear 733 and the fourth rack gear 743 fastened to the first plate 630 may also move in a direction in which the first plate 630 is withdrawn. Accordingly, the first pinion gear 731 and the second pinion gear 741 disposed to interlock with the second rack gear 733 and the fourth rack gear 743 may rotate in opposite directions. When the first pinion gear 731 and the second pinion gear 741 rotate in opposite directions, the first rack gear 732 and the third rack gear 742 disposed to interlock with the first pinion gear 731 and the second pinion gear 741, respectively, may also move in a direction opposite to the direction in which the first plate 630 is withdrawn. Accordingly, the second plate 650 fastened to the first rack gear 732 and the third rack gear 742 may also symmetrically move in the direction opposite to the direction in which the first plate 630 is withdrawn. As shown above, since the first plate 630 and the second plate 650 are connected and slide together, the large area X-ray detecting device 470 may be disposed on the central portion of the base 620, and thus, the arrangement of the object 10 and the large area X-ray detecting device 470 may be accomplished in the table-type X-ray imaging apparatus 200.

Figure 15:
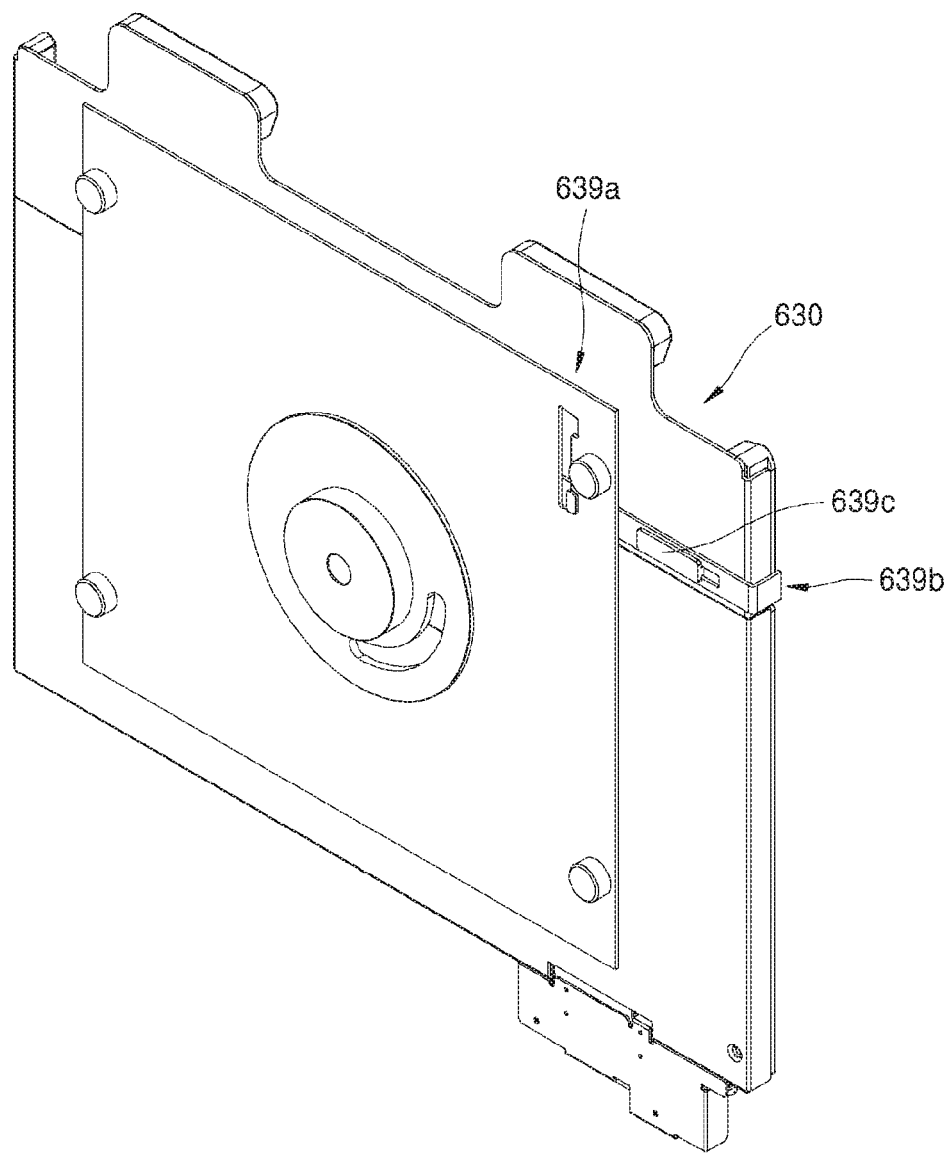
FIG. 15 is a rear perspective view of a first plate according to an exemplary embodiment.
Figure 16A:
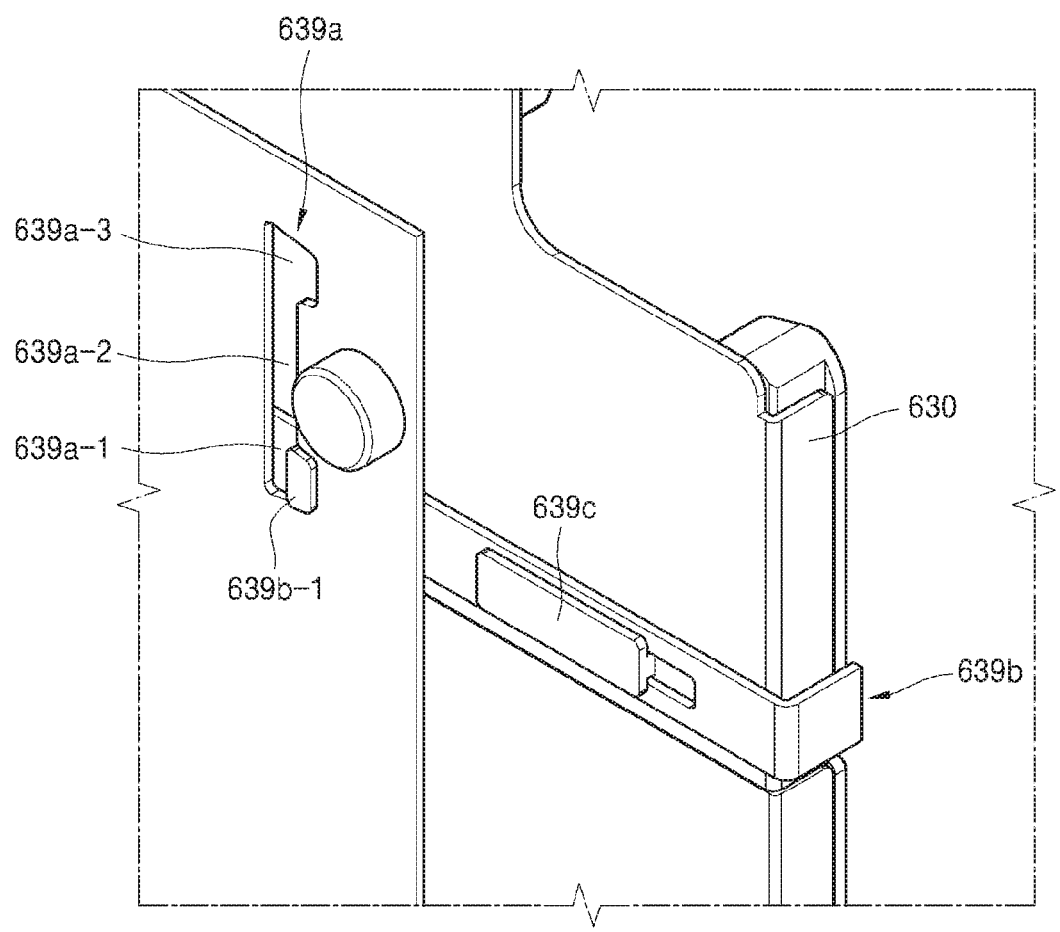
FIGS. 16A, 16B, and 16C are partial perspective views of a portion of the first plate of FIG. 15.
Figure 16B:
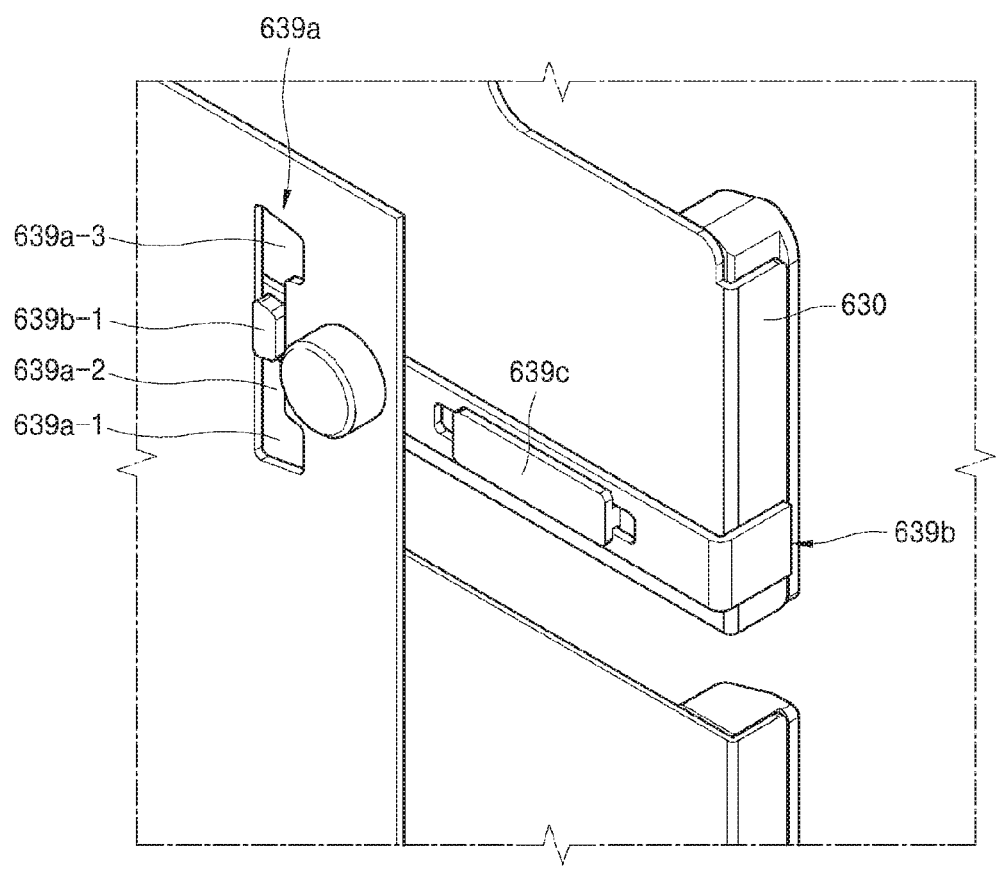

FIG. 15 is a rear perspective view of the first plate 630 according to an exemplary embodiment, and FIGS. 16A and 16B are partial perspective views of a portion of the first plate 630 of FIG. 15.

When the accommodation or the discharge of the second plate 650 with respect to the first plate 630 is completed, a relative location of the second plate 650 with respect to the first plate 630 has to be fixed, and thus, the arrangement of the X-ray detecting device 400 and the object 10 may be maintained.

Referring to FIG. 15, while a third slide fastener 639a is fastened to the middle plate 660 illustrated in FIG. 12, the third slide fastener 639a may be disposed at a rear surface portion of the first plate 630 to provide a slide portion that is substantially ⊏ shaped. A fourth slide fastener 639b may be disposed to move in a direction by using a clamping guide 639c fastened to the first plate 630, and may be disposed to be restored to an original position thereof when an external pressure is released after the fourth slide fastener 639a moves in a direction by the external pressure, by using an elastic member (not shown). When the external pressure is not applied to the fourth slide fastener 639b, the fourth slide fastener 639b is supported by an end of the third slide fastener 639a, and thus, a movement of the fourth slide fastener 639b is blocked. When the external pressure is applied to the fourth slide fastener 639b, a support of the fourth slide fastener 639b by the end of the third slide fastener 639a is released, and thus, the fourth slide fastener 639b may move in a direction in which the first plate 630 is withdrawn, as described in more detail below with reference to FIGS. 16A through 16C.

Referring to FIG. 16A, when an external pressure is not applied to the fourth slide fastener 639b, a protrusion 639b-1 of the fourth slide fastener 639b is supported by an end 639a-1 of the third slide fastener 639a, and in this case, a relative position of the first plate 630 with respect to the base 620 is fixed, and thus, the first plate 630 does not slide with respect to the second plate 650.

Referring to FIG. 16B, when an external pressure is applied to the fourth slide fastener 639b, the end 639a-1 of the third slide fastener 639a may move inwardly towards the first plate 630, and thus, the support between the protrusion 639b-1 of the fourth slide fastener 639b and the end 639a-1 of the third slide fastener 639a may be released. Accordingly, the protrusion 639b-1 of the fourth slide fastener 639b may move along a middle slide unit 639a-2 extending in the direction in which the first plate 630 is withdrawn. In this case, the first plate 630 does not slide with respect to the second plate 650.

Figure 16C:
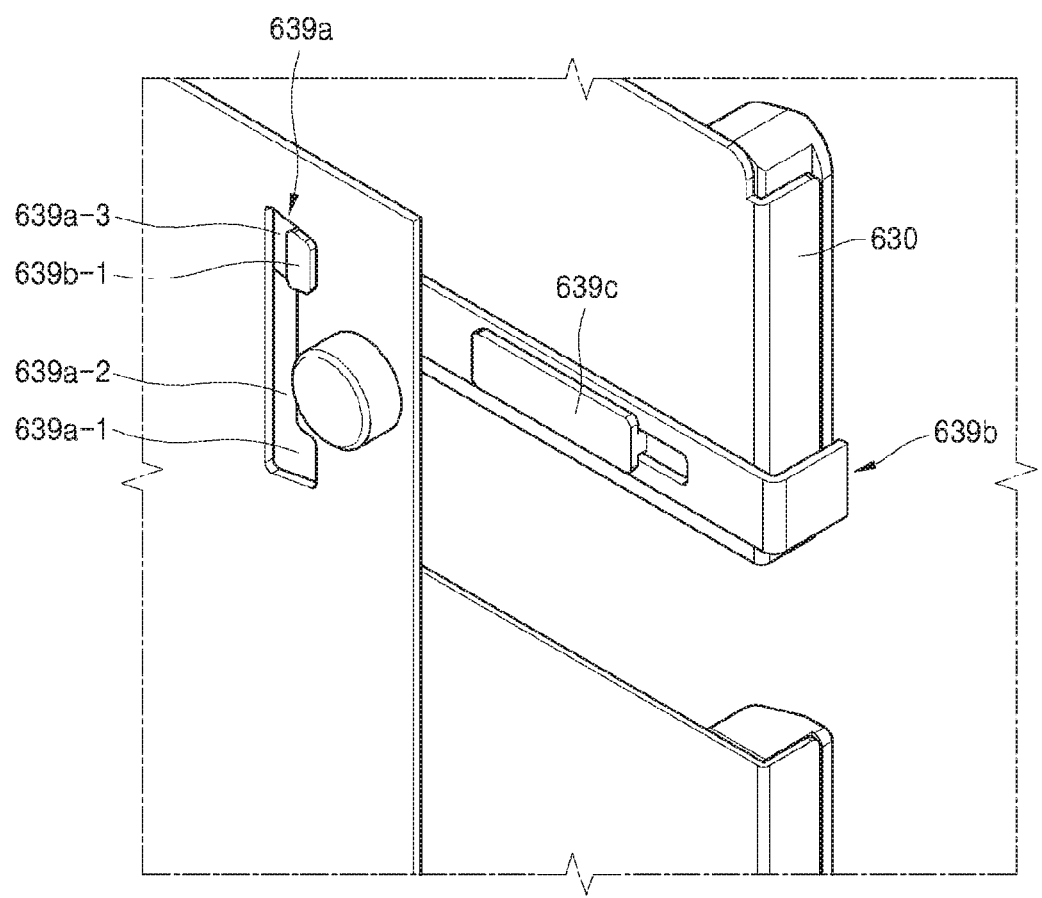

Referring to FIG. 16C, when the withdrawal of the first plate 630 with respect to the second plate 650 is completed, the protrusion 639b-1 of the fourth slide fastener 639b may be supported by the other end 639a-3 of the third slide fastener 639a, and thus, the first plate 630 may be fixed at a position at which the first plate 630 is withdrawn from the second plate 650.

Figure 17:
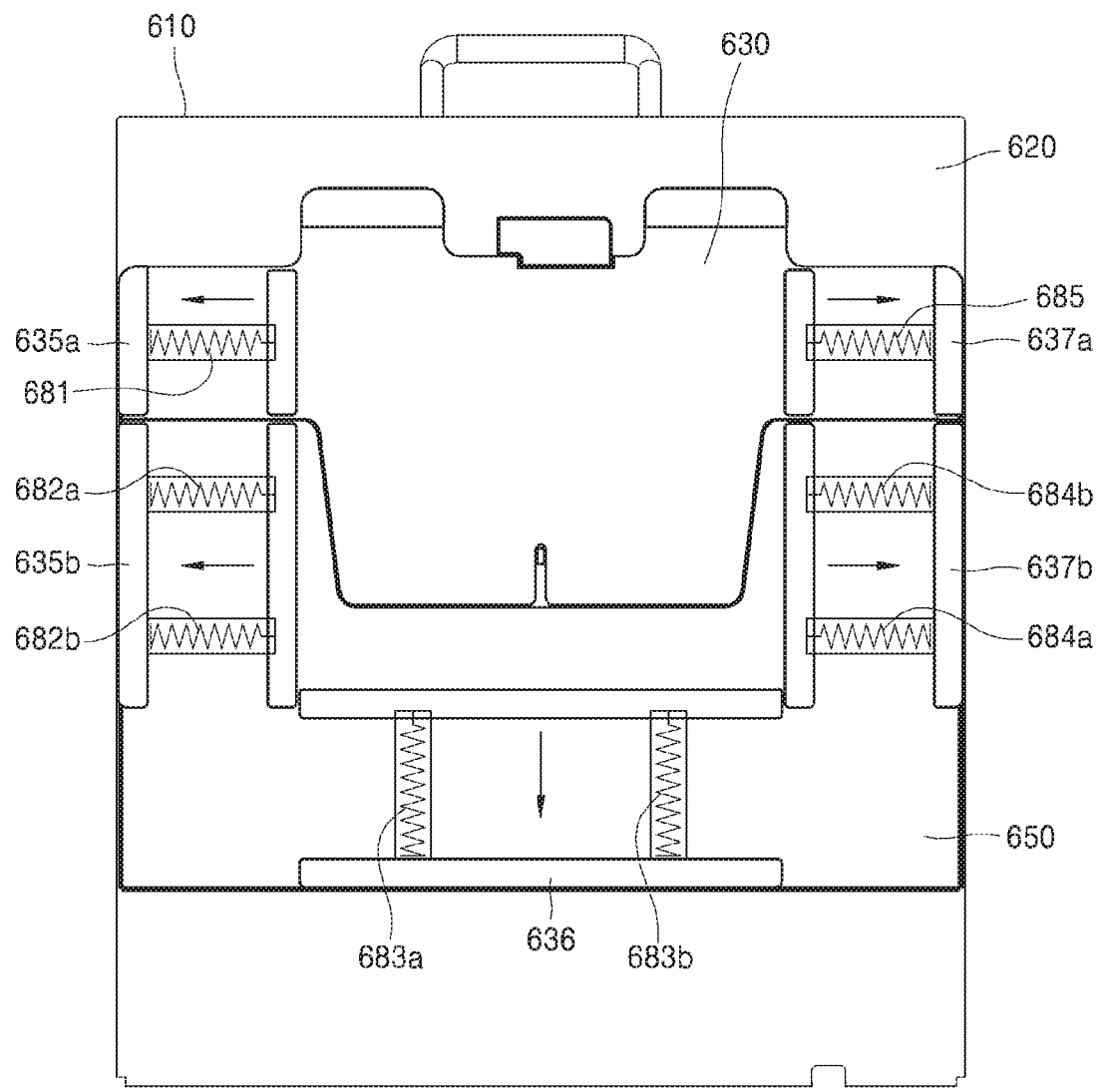
FIG. 17 is a plan view of a bucky tray according to an exemplary embodiment.

FIG. 17 is a plan view of the bucky tray 610 according to an exemplary embodiment.

As described above, the X-ray detecting device 400 according to an exemplary embodiment may include a relative large incident area or a relatively small incident area.

Referring to FIG. 17, for example, the small area X-ray detecting device 460 may be disposed on the bucky tray 610. To fasten the small area X-ray detecting device 460 on the first plate 630, first location guides 635a and 635b, a second location guide 636, and third location guides 637a and 637b may be disposed on the first plate 630 to be slidable, and each of the location guides may move by the plurality of elastic members 681, 682a, 682b, 683a, 683b, 684a, 684b, and 685. As the first location guides 635a and 635b and the third location guides 637a and 637b symmetrically slide, the small area X-ray detecting device 460 having a relatively small incident area may be disposed at a central portion of the first plate 630, and thus, the arrangement of the object 10 and the X-ray detecting device may be achieved. The method in which the plurality of guides 635 through 637 slide by the plurality of elastic members 681 through 685 is substantially the same as the method described in FIGS. 9A through 9C, and thus, its description will be omitted.

Figure 18A:
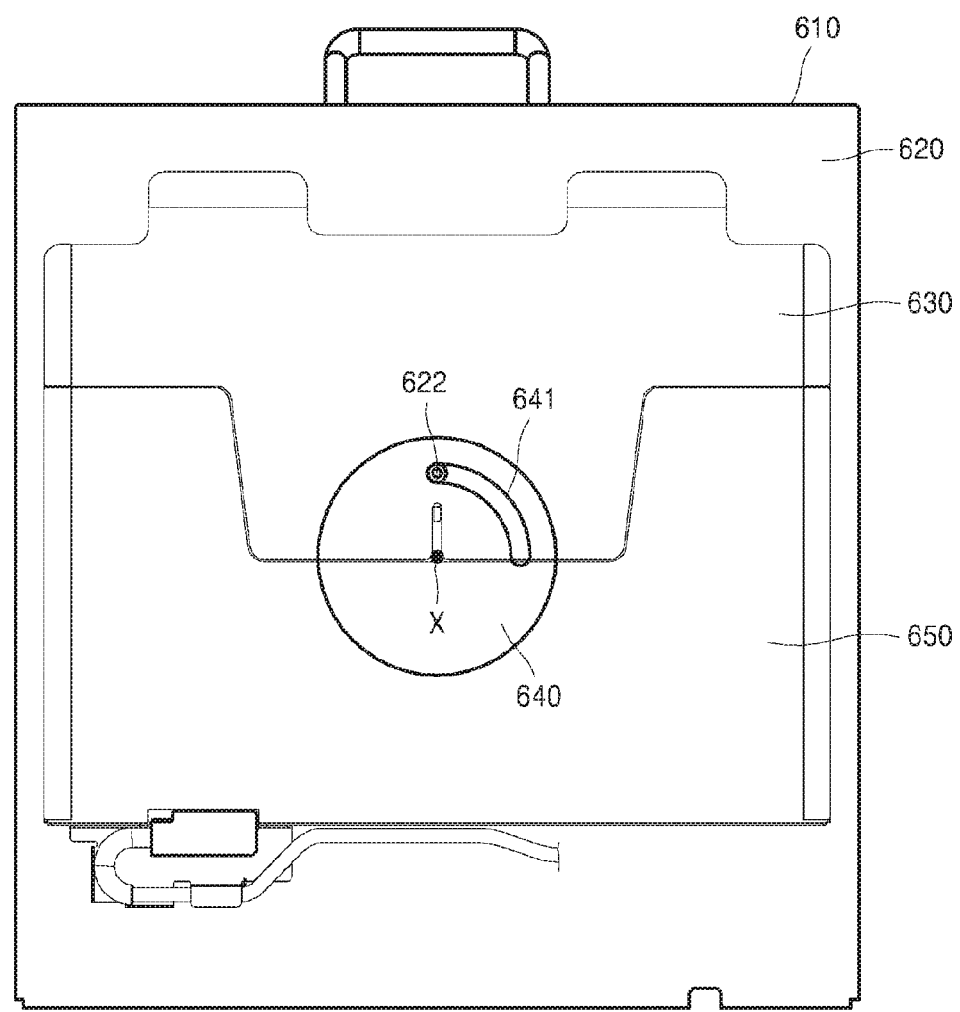
FIGS. 18A and 18B are plan views of a bucky tray according to an exemplary embodiment.
Figure 18B:
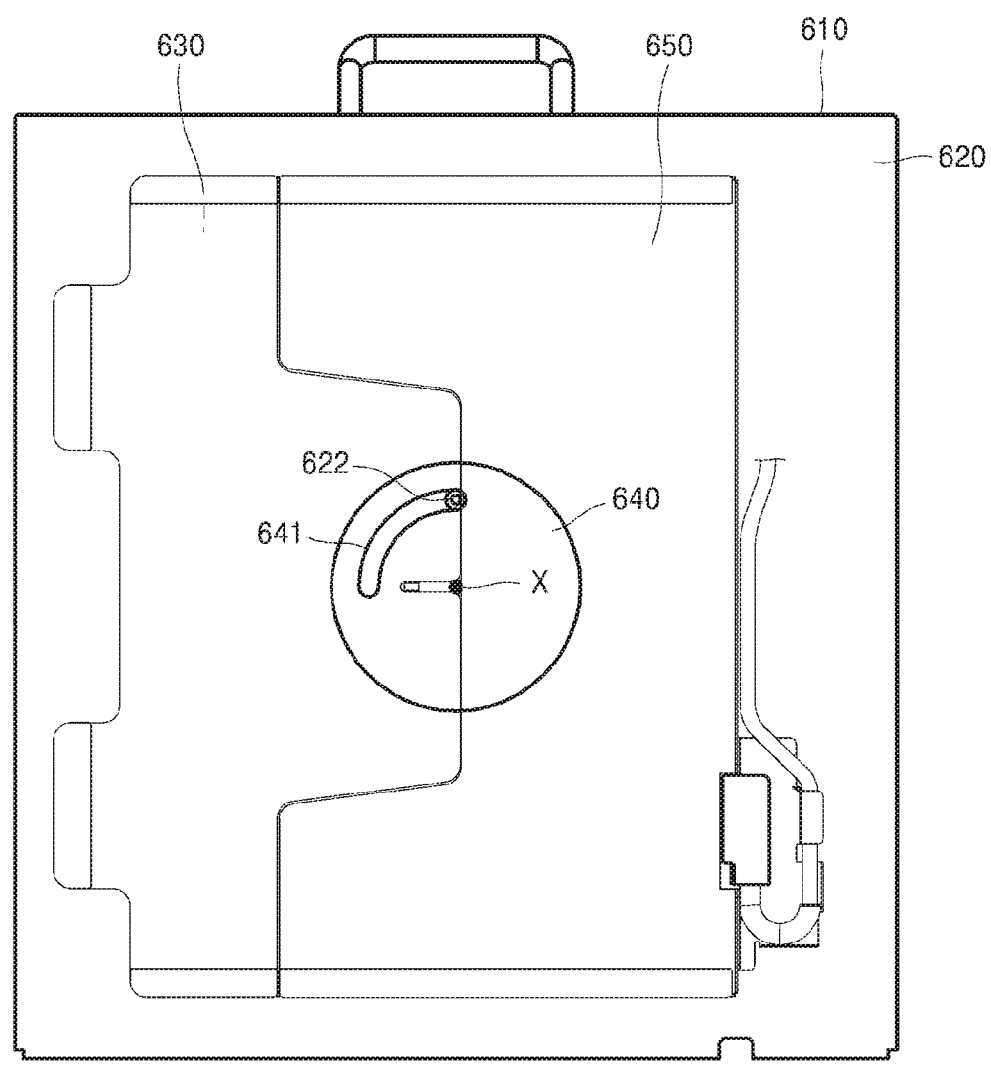

FIGS. 18A and 18B are plan views of the bucky tray 610 according to an exemplary embodiment.

Referring to FIGS. 18A and 18B, the X-ray detecting device 400 may be disposed on the bucky tray 610 to be rotatable. The first plate 630 and the second plate 650 are fastened to the rotation plate 640, and thus, the first plate 630 and the second plate 650 may rotate and the X-ray detecting device 400 supported by the first plate 630 and the second plate 650 may rotate. The center of the central member 621 may correspond to the center X of the base 620. Accordingly, the rotated X-ray detecting device 400 may also be disposed on a central portion of the first plate 630, and the arrangement of the object 10 and the X-ray detecting device 400 may be achieved. The method in which the first plate 630 and the second plate 650 rotate by the rotation plate 640 is the same as the method described in FIGS. 6A and 7A, and thus, its description will be omitted.

Figure 19:
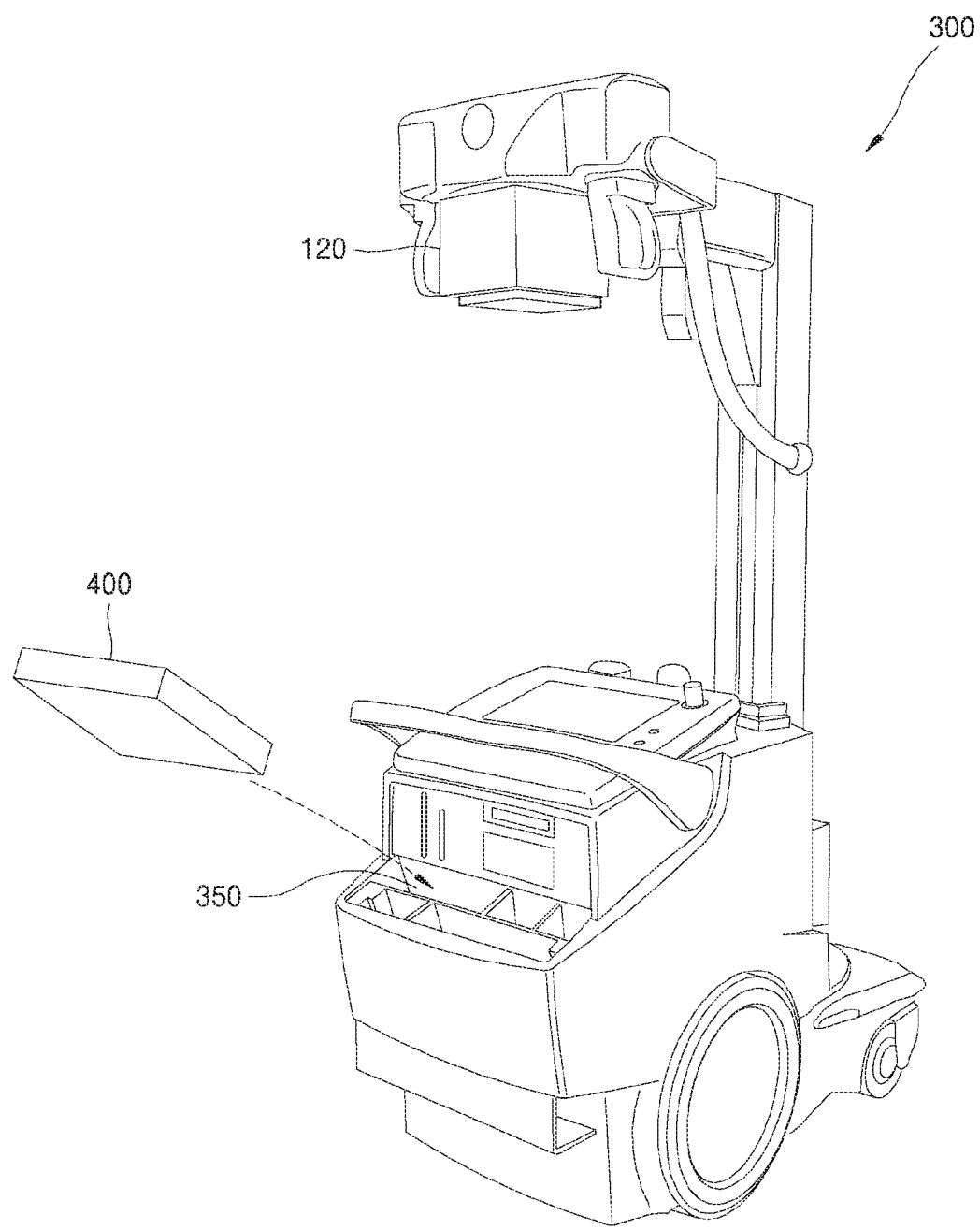
FIG. 19 is a perspective view of a mobile X-ray imaging apparatus, according to an exemplary embodiment.
Figure 20:
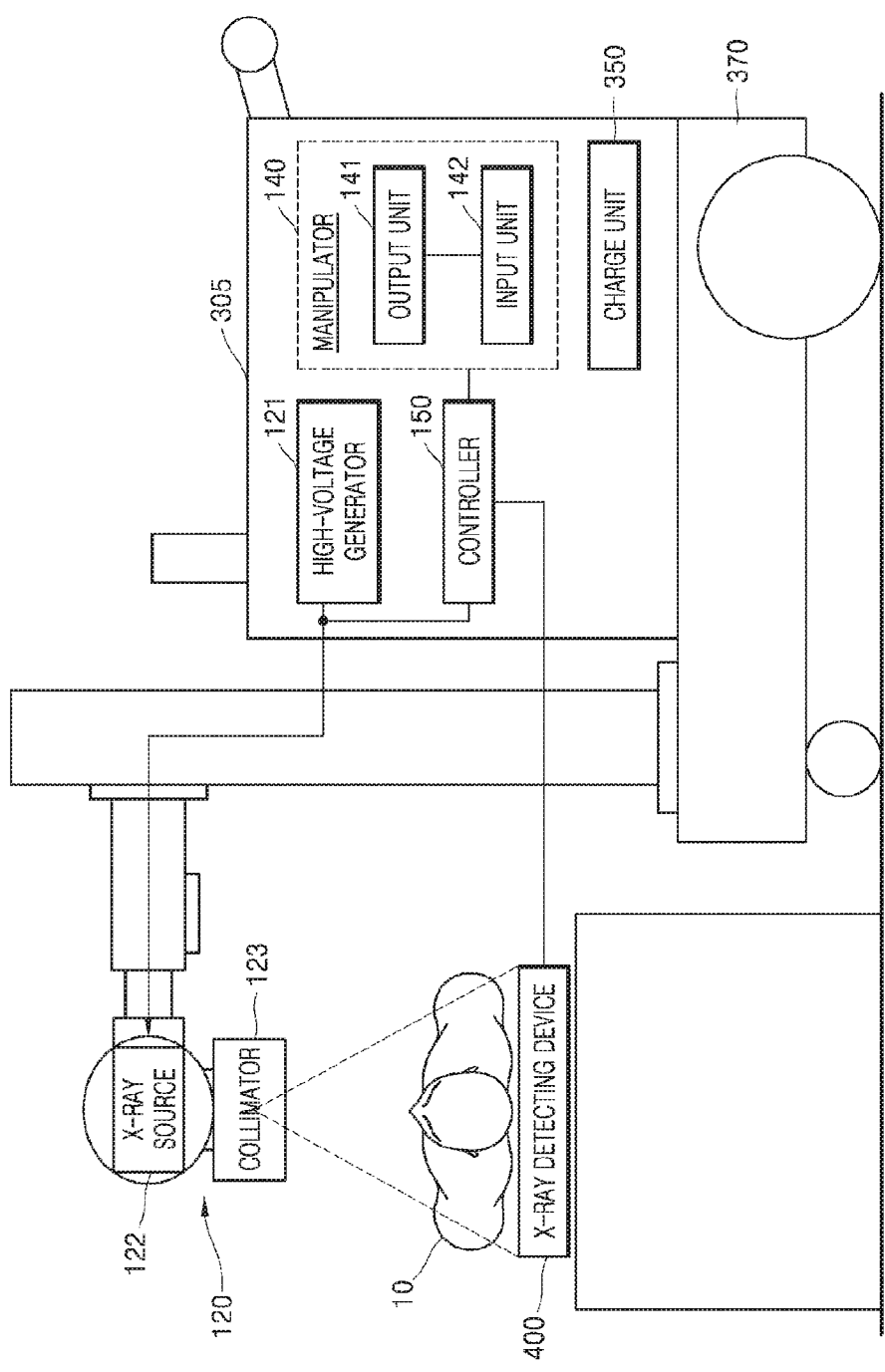
FIG. 20 is a block diagram of the mobile X-ray imaging apparatus of FIG. 19.

FIG. 19 is a perspective view of a mobile X-ray imaging apparatus 300 capable of performing X-ray imaging regardless of imaging locations, according to an exemplary embodiment, and FIG. 20 is a block diagram of the mobile X-ray imaging apparatus 300 of FIG. 19.

Referring to FIGS. 19 and 20, the mobile X-ray imaging apparatus 300 includes a main unit 305 which includes a moving unit 370 including a wheel for a movement of the X-ray imaging apparatus 300, a manipulator including an input unit 142 for receiving a command for manipulating the X-ray imaging apparatus 300, a high-voltage generator 121 for generating a high voltage to be applied to the X-ray source 122, a sound output unit 141 for outputting a sound indicating imaging-related information, such as an X-ray emission, and a controller 150 for controlling operations of the X-ray imaging apparatus 300. The X-ray emitter 120 includes the X-ray source 122 for generating X-rays, and a collimator 123 for guiding a path of the X-rays generated and emitted from the X-ray source 122. The X-ray detecting device 400 detects the X-rays which were emitted from the X-ray emitter 120 and have penetrated an object.

The input unit 142 may include various input devices, as described above with reference to the input units 112 and 142 of FIG. 1. A user may input a command for emitting X-rays via a switch and the X-ray emission and detection may proceed as described above with reference to FIG. 1.

When the emission signal is output from the input unit 142, the controller 150 may output a sound output signal to the sound output unit 141 for the sound output unit 141 to output a predetermined sound, so that the X-ray emission is informed to the object. The sound output unit 141 may output a sound which indicates other types of imaging-related information than the X-ray emission.

Although FIG. 20 illustrates that the sound output unit 141 is included in the main unit 305, it is not limited thereto. For example, the sound output unit 141 may be located where the mobile X-ray imaging apparatus 300 is located. For example, the sound output unit 141 may be located on a wall of a patient's room.

The controller 150 controls locations of the X-ray emitter 120 and the X-ray detecting device 400, and imaging timings and conditions, according to predetermined imaging conditions.

The controller 150 generates a medical image of the object by using image data received from the X-ray detecting device 400. In detail, the controller 150 may receive the image data from the X-ray detecting device 400, remove noise from the image data, and generate the medical image of the object by adjusting a dynamic range and interleaving.

The main unit 305 of the mobile X-ray imaging apparatus 300 may further include an output unit (not shown) configured to output the medical image generated by the controller 150, and the charge unit 350. The output unit may output a user interface (UI), user information, or object information that a user needs to manipulate the X-ray imaging apparatus 300.

The charge unit 350 is a charge member for charging the X-ray detecting device 400 while the X-ray detecting device 400 is not used. In the mobile X-ray imaging apparatus 300, the X-ray detecting device 400 may be disposed at random positions while not being mounted in the bucky 500 and 600. Thus, the X-ray detecting device 400 used in the mobile X-ray imaging apparatus 300 has to be charged prior to an imaging performance. The charge unit 350 used in the mobile X-ray imaging apparatus 300 may be a storage unit for storing the X-ray detecting device 400.

As described above, the X-ray imaging apparatus 300 may have different diagnostic areas according to diagnostic purposes, and may emit X-rays to a relatively large area or a relatively small area according to the diagnostic area. Thus, the X-ray detecting device 400 may be formed to have not only a relatively large incident area but also a relatively small incident area, and thus, the charge unit 350 may accommodate not only the large area X-ray detecting device 470 but also the small area X-ray detecting device 460.

Figure 21:
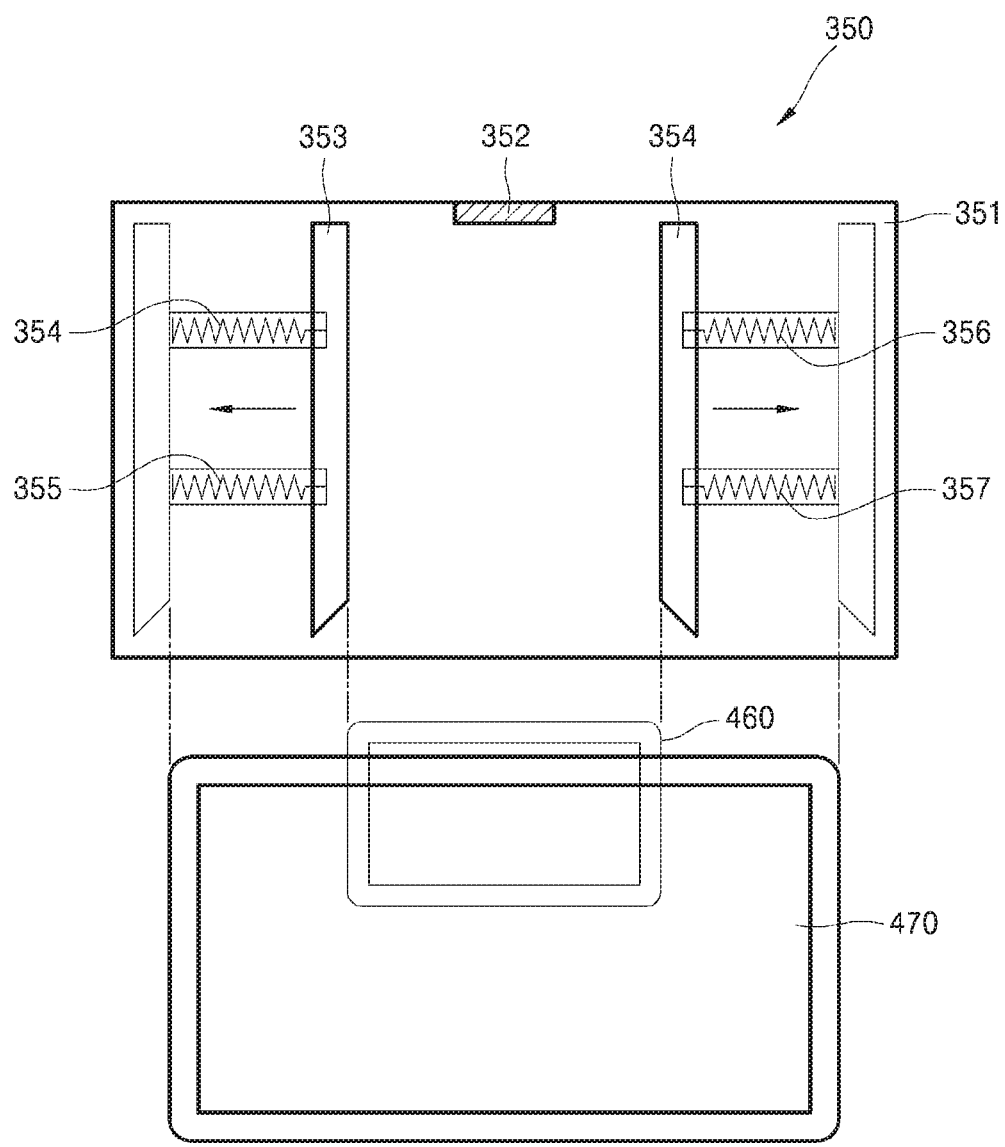
FIG. 21 is a plan view of a charge unit according to an exemplary embodiment.

FIG. 21 is a plan view of the charge unit 350 according to an exemplary embodiment.

Referring to FIG. 21, the charge unit 350 may include a charge base 351 for supporting the X-ray detecting device 400, a charge terminal 352 which may be coupled to the first terminal 421 of the X-ray detecting device, first and second supporting guides 353 and 354 disposed on the charge base 351 to be slidable, and the plurality of elastic members 354 through 357, an end of each of which is connected to the first and second supporting guide units 353 and 354 and the other end of each of which is fastened to the charge base unit 351.

An end of the first and second supporting guides 353 and 354 may form a predetermined angle with respect to a direction in which the small area and the large area X-ray detecting devices 460 and 470 are introduced. An end of the first and second elastic members 354 and 355 may be fastened to the charge base 351 and the other end of the first and second elastic members 354 and 355 may be fastened to the first supporting guide 353. The first and second elastic members 354 and 355 may be disposed symmetrically with a predetermined distance therebetween. An end of the third and fourth elastic members 356 and 357 may be fastened to the charge base 351 and the other end of the third and fourth elastic members 356 and 357 may be fastened to the second supporting guide 354. The third and fourth elastic members 356 and 357 may be disposed symmetrically with a predetermined distance therebetween.

When the small area X-ray detecting device 460 is disposed on the charge base 351, the first through fourth elastic members 355 through 357 are not be compressed, and thus, the first supporting guide 353 and the second supporting guide 354 do not slide and may support the small area X-ray detecting device 460 on the charge base 351. On the contrary, when the large area X-ray detecting device 470 is disposed on the charge base 351, the first through fourth elastic members 355 through 357 may be compressed, and thus, the first supporting guide 353 and the second supporting guide 354 may slide and may support the large area X-ray detecting device 470 on the charge base 351.

The small area X-ray detecting device 460 and the large area X-ray detecting device 470 are described above as a non-limiting example only. In an exemplary embodiment, the X-ray detecting devices of various sizes may be similarly accommodated and stored in the charge unit 350, and the charge terminal 352 included in the charge unit 350 may charge the X-ray detecting devices by being coupled to the first terminal 421 of the X-ray detecting device or the X-ray detecting devices may be charged wirelessly, as described above with reference to FIGS. 5E and 5F.

As described above, according to exemplary embodiments, the arrangement of the X-ray detecting device in the bucky may be changed, and thus, an angle at which the X-ray detecting device is used can be more easily adjusted.

Also, since a plurality of plates are used, X-ray detecting devices of various sizes can be arranged in a single bucky tray.

The foregoing exemplary embodiments and advantages are merely exemplary and are not to be construed as limiting. The present teaching may be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bucky tray for an X-ray imaging apparatus, the bucky tray comprising:
a first plate comprising a first surface, wherein a bottom surface of a first X-ray detecting device of a first size or a bottom surface of a second X-ray detecting device of a second size is mountable on the first surface; and a second plate which is configured to be coupled to the first plate and to be movable to at least one of a first location where the first X-ray detecting device is to be accommodated and a second location where the second X-ray detecting device of a is to be accommodated, the second plate comprising a second surface aligned with the first surface of the first plate as an extension of the first surface to provide a supporting structure, wherein the bottom surface of the first X-ray detecting device or the bottom surface of the second X-ray detecting device is supported by the second surface of the second plate in response to the second plate being moved to the first location or the second location, respectively, and wherein the first plate and the second plate are configured to symmetrically move in opposite directions.

2. The bucky tray of claim 1, further comprising a base, wherein the first plate and the second plate are configured to be rotatable with respect to the base.

3. The bucky tray of claim 1, further comprising:
a base;
a middle plate positioned between the base and one of the first plate and the second plate;
a rotation axis positioned on the middle plate;
a pair of slide rails disposed on opposite sides of and apart from the rotation axis; and
a pair of guides respectively positioned on the first plate and the second plate,
wherein the pair of slide rails are configured to be rotatable with respect to the rotation axis, and the pair of guides are configured to respectively move in the pair of slide rails.

4. The bucky tray of claim 1, further comprising:
a base;
a middle plate positioned between the first plate and the base;
a pinion gear positioned on the middle plate; and
a pair of rack gears respectively positioned on the first plate and the second plate and interlocked to the pinion gear.

5. The bucky tray of claim 1, further comprising:
location guides configured to guide a location of the first X-ray detecting device or the second X-ray detecting device such that a center of the bucky tray matches a center of the first X-ray detecting device or a center of the second X-ray detecting device,
wherein at least one of the location guides is provided on the second plate.

6. The bucky tray of claim 1, further comprising a slide fastener configured to fasten the second plate in the first location and the second location.

7. The bucky tray of claim 2, further comprising a rotation plate positioned between the first plate and the base and coupled to the first plate so that the rotation plate is rotatable together with the first plate and the second plate.

8. The bucky tray of claim 7, further comprising one or more rotation sensors configured to sense a rotation position of the rotation plate after the rotation plate is rotated.

9. The bucky tray of claim 8, wherein the one or more rotation sensors comprise:
a first rotation sensor; and
a second rotation sensor arranged apart from each other by a predetermined distance along a cylindrical direction of the rotation plate.

10. The bucky tray of claim 9, wherein each of the first rotation sensor and the second rotation sensor includes an optical encoder or a magnetic encoder.

11. The bucky tray of claim 1, further comprising:
a detachment sensor configured to sense whether the first X-ray detecting device or the second X-ray detecting device is attached to or detached from the bucky tray.

12. The bucky tray of claim 7, wherein a center of the rotation plate is eccentric with respect to a center of the base.

13. The bucky tray of claim 7, wherein a center of the rotation plate matches a center of the base.

14. An X-ray imaging apparatus comprising:
a first X-ray detecting device of a first size or a second X-ray detecting device of a second size;
a bucky tray on which the first X-ray detecting device or the second X-ray detecting device is to be mounted; and
an accommodation unit configured to accommodate the bucky tray,
wherein the bucky tray is configured to be accommodated in or discharged from the accommodation unit and comprises:
a first plate comprising a first surface, a bottom surface of the first X-ray detecting device or a bottom surface of the second X-ray detecting device being mountable on the first surface, and
a second plate which is configured to be coupled to the first plate and to be movable to at least one of a first location where the first X-ray detecting device is to be accommodated and a second location where the second X-ray detecting device of a second size is to be accommodated, the second plate comprising a second surface aligned with the first surface of the first plate as an extension of the first surface to provide a supporting structure,
wherein the bottom surface of the first X-ray detecting device or the bottom surface of the second X-ray detecting device is supported by the second surface of the second plate in response to the second plate being moved to the first location or the second location, respectively, and
wherein the first plate and the second plate are configured to symmetrically move in opposite directions.

15. The X-ray imaging apparatus of claim 14, further comprising a slide fastener configured to fasten the second plate in the first location and the second location.

16. The X-ray imaging apparatus of claim 14, wherein the bucky tray further comprises:
a base;
a middle plate positioned between the base and one of the first plate and the second plate;
a rotation axis positioned on the middle plate;
a pair of slide rails disposed on opposite sides of and apart from the rotation axis; and
a pair of guides respectively positioned on the first plate and the second plate,
wherein the pair of slide rails is configured to be rotatable with respect to the rotation axis, and
the pair of guides is configured to respectively move in the pair of slide rails.

17. The X-ray imaging apparatus of claim 14, further comprising:
a wireless charger interacting with a battery included in the first X-ray detecting device or the second X-ray detecting device.

18. The bucky tray of claim 1, further comprising:
a base;
a middle plate which is positioned between the base and at least one among the first plate and the second plate; and
a movement guide which includes a first portion fastened to the first plate, a second portion fastened to the second plate, and a third portion fastened to the middle plate, wherein the first plate and the second plate are configured to move with respect to one another by moving the first portion and the second portion in opposite directions with respect to a position of the third portion.

19. The X-ray imaging apparatus of claim 14, wherein the bucky tray further comprises:
   a base; and
   a rotation plate positioned between the first plate and the base and coupled to the first plate so that the rotation plate is rotatable together with the first plate and the second plate.

20. The X-ray imaging apparatus of claim 19, further comprising:
   one or more rotation sensors configured to sense a rotation position of the rotation plate after the rotation plate is rotated.

21. The X-ray imaging apparatus of claim 20, wherein the one or more rotation sensors comprise:
   a first rotation sensor; and
   a second rotation sensor arranged apart from each other by a predetermined distance along a cylindrical direction of the rotation plate.

22. The X-ray imaging apparatus of claim 20, further comprising:
   a controller configured to receive, from the one or more rotation sensors, a sensing signal indicating an arrangement location of the first X-ray detecting device or the second X-ray detecting device based on the rotation position of the rotation plate and transmit a control signal regarding a size of an X-ray exposure area to an X-ray emitter.

* * * * *